US009439906B2

(12) United States Patent
Vermeulen et al.

(10) Patent No.: US 9,439,906 B2
(45) Date of Patent: Sep. 13, 2016

(54) DOSING REGIMEN ASSOCIATED WITH LONG ACTING INJECTABLE PALIPERIDONE ESTERS

(75) Inventors: An Vermeulen, Beerse (BE); Alfons Wouters, Beerse (BE)

(73) Assignee: Janssen Pharmaceutica NV (BE)

( * ) Notice: Subject to any disclaimer, the term of this patent is extended or adjusted under 35 U.S.C. 154(b) by 770 days.

(21) Appl. No.: 12/337,144

(22) Filed: Dec. 17, 2008

(65) Prior Publication Data

US 2009/0163519 A1   Jun. 25, 2009

Related U.S. Application Data

(60) Provisional application No. 61/014,918, filed on Dec. 19, 2007, provisional application No. 61/120,276, filed on Dec. 5, 2008.

(51) Int. Cl.
| | | |
|---|---|---|
| C07D 471/04 | (2006.01) | |
| A61K 31/445 | (2006.01) | |
| A61K 31/41 | (2006.01) | |
| A61K 31/42 | (2006.01) | |
| A61K 31/519 | (2006.01) | |

(52) U.S. Cl.
CPC .................................. *A61K 31/519* (2013.01)

(58) Field of Classification Search
CPC . A61K 31/519; A61K 9/0019; A61K 9/0024
USPC .................................. 514/257, 323, 360, 379
See application file for complete search history.

(56) References Cited

U.S. PATENT DOCUMENTS

| | | | |
|---|---|---|---|
| 4,804,663 | A | 2/1989 | Kennis et al. |
| 5,158,952 | A | 10/1992 | Janssen et al. |
| 5,254,556 | A | 10/1993 | Janssen et al. |
| 5,453,425 | A | 9/1995 | Francois et al. |
| 5,612,346 | A | 3/1997 | Mesens et al. |
| 6,077,843 | A | 6/2000 | François et al. |
| 6,555,544 | B2 | 4/2003 | François et al. |
| 6,577,545 | B2 | 6/2003 | Kim et al. |
| 2002/0082245 | A1 | 6/2002 | Yelle |
| 2003/0157180 | A1 | 8/2003 | Francois et al. |
| 2007/0197591 | A1 | 8/2007 | Boom et al. |
| 2009/0163519 | A1 | 6/2009 | Vermeulen et al. |
| 2011/0105536 | A1 | 5/2011 | Lewyn-Briscoe et al. |
| 2012/0263795 | A1 | 10/2012 | Francois et al. |

FOREIGN PATENT DOCUMENTS

| | | |
|---|---|---|
| WO | 2004/010981 | 2/2004 |
| WO | WO 2006/114384 | 11/2006 |
| WO | 2008/021342 | 2/2008 |
| WO | 2009/025859 | 2/2009 |
| WO | 2009/047499 | 4/2009 |
| WO | 2009/080651 | 7/2009 |
| WO | 2011/053829 | 5/2011 |

OTHER PUBLICATIONS

Alphs L, Bossie C, Sliwa JK, Ma YW, Haskins T Tolerability of Paliperidone Palmitate Initiation Doses in Subjects With Recently Diagnosed Schizophrenia. Poster No. NR6-21 at the 163rd Annual Meeting of the American Psychiatric Association (APA), New Orleans, Louisiana, USA, May 22-26, 2010.

Alphs L, Haskins, Bossie C, Sliwa JK, Gopal S, Hough D, Davis J Long-term Metabolic Outcomes With Paliperidone Palmitate, A Once-Monthly Long-Acting Injectable Antipsychotic Agent, in the Treatment of Subjects With Schizophrenia. Poster No. 204 at the 48th Annual Meeting of the American College of Neuropsychopharmacology (ACNP), Hollywood, Florida, USA, December 6-10, 2009.

Cleton A, Rossenu S, Crauwels H, Berwaerts J, Hough D, Gopal S, Eerdekens M, Vandebosch A, Rosso Fernandez C Assessment of the Dose Proportionality of Paliperidone Palmitate 25, 50, 100 and 150 mg eq., A New Long-Acting Injectable Antipsychotic, Following Administration in the Deltoid or Gluteal Muscles. Poster at the 2008 Annual Meeting of the American Society for Clinical Pharmacology and Therapeutics (ASCPT), Orlando, Florida, USA, Apr. 2-5, 2008.

Coppola D, Liu Y, Gopal S, Remmerie B, Samtani M, Pandina G, Hough D, Nuamah I, Sulaiman A Long-Term Safety, Tolerability and Pharmacokinetics of Paliperidone Palmitate 234 mg (150 mg eq.), The Highest Marketed Dose: A One-Year Open-Label Study in Patients With Schizophrenia. Poster No. PI-49 at the 2010 Annual Meeting of the American Society for Clinical Pharmacology and Therapeutics (ASCPT), Atlanta, Georgia, USA, Mar. 17-20, 2010.

Gopal S, Berwaerts J, Nuamah I, Akhras K, Coppola D, Daly E, Hough DW, Palumbo JM Efficacy and Safety of Long-Acting Injectable Paliperidone Palmitate Relative to Long-Acting Haloperidol, Bromperidol and Fluphenazine Decanoate for Long-Term Treatment in Patients With Schizophrenia Using Number Needed to Treat and Number Needed to Harm. Poster at the 65th Annual Convention and Scientific Program of the Society of Biological Psychiatry (SOBP), New Orleans, Louisiana, USA, May 20-22, 2010.

Gopal S, Gassmann-Mayer C, Palumbo J, Samtani MN, Shiwach R, Alphs L, Practical Guidance for Dosing and Switching Paliperidone Palmitate Treatment in Patients with Schizophrenia, Current Medical Research and Opinion 26 (2), p. 377-387, 2010.

Gopal S, Hough DW, Xu H, Lull JM, Gassmann-Mayer C, Remmerie BM, Eerdekens MH, Brown DW, Efficacy and Safety of Paliperidone Palmitate in Adult Patients with Acutely Symptomatic Schizophrenia: A Randomized, Double-Blind, Placebo-Controlled, Dose-Response Study, International Clinical Psychopharmacology, pp. 247-256 (2010).

Gopal S, Lindenmayer JP, Hough D, Melkote R, Lim P, Eerdekens M, Safety and Tolerability of the Investigational Antipsychotic Paliperidone Palmitate Injected in the Deltoid or Gluteus Muscle in Patients with Schizophrenia, 63rd Annual Convention and Scientific Program of the Society of Biological Psychiatry (SOBP), Washington, DC, USA, May 1-3, 2008, Biological Psychiatry 63 (7, Suppl. 7), p. 285S, 2008.

Gopal S, Vijapurkar U, Lim P, Morozova M, Eerdekens M Long-Term Efficacy, Safety and Tolerability of Paliperidone Palmitate in Patients with Schizophrenia. Poster No. 20 at the 12th Annual Meeting of the College of Psychiatric and Neurologic Pharmacists (CPNP), Jacksonville, Florida, Apr. 19-22, 2009.

(Continued)

*Primary Examiner* — Sreeni Padmanabhan
*Assistant Examiner* — Jody Karol

(57) ABSTRACT

The present invention provides a method of treating patients in need of treatment with long acting injectable paliperidone palmitate formulations.

21 Claims, 3 Drawing Sheets

(56) References Cited

OTHER PUBLICATIONS

Haskins JT, Sliwa JK, Ma YW, Pandina GJ, Palumbo J Efficacy and Safety of 234 mg Initation Dose and 3-Fixed Maintenance Doses of Paliperidone Palmitate—A Once-Monthly Injectable Atypical Antipsychotic. Poster No. 123 at the 22nd US Psychiatric and Mental Health Congress (USPMHC), Las Vegas, Nevada, USA, Nov. 2-5, 2009.

Hough D, Gopal S, Vijapurkar U, Lim P, Morozova M, Eerdekens M Paliperidone Palmitate, an Atypical Injectable Antipsychotic, In Prevention of Symptom Recurrence in Patients with Schizophrenia: A Randomized, Double-Blind, Placebo Controlled Study. Poster at the 63rd Annual Convention and Scientific Program of the Society of Biological Psychiatry (SOBP), Washington, DC, USA, May 1-3, 2008.

Hough D, Gopal S, Vijapurkar U, Lim P, Morozova M, Eerdekens M, Paliperidone Palmitate in Prevention of Symptom Recurrence in Patients with Schizophrenia: A Randomized, Double-Blind, Placebo-Controlled Study, 161st Meeting of the American Psychiatric Association (APA), Washington, DC, USA, May 3-8, 2008, Proceedings/AbstractBook, p. 173, No. NR4-029, 2008.

Hough D, Lindenmayer JP, Gopal S, Melkote R, Lim P, Herben V, Yuen E, Eerdekens M, Safety and Tolerability of Deltoid and Gluteal Injections of Paliperidone Palmitate in Schizophrenia, Progress in Neuro-Psychopharmacology and Biological Psychiatry 33 (6), p. 1022-1031, 2009.

Kozma C, Dirani R, Nicholl D, Akhras K Evaluation of the Relationships Among Change in Function, Symptoms, and Duration of Schizophrena. Poster No. NR6-4 at the 163rd Annual Meeting of the American Psychiatric Association (APA), New Orleans, Louisiana, USA, May 22-26, 2010.

Kramer M, Litman R, Hough D, Lane R, Lim P, Eerdekens M A 9-Week, Placebo-Controlled Study in Schizophrenia Patients: Efficacy and Safety of the Long-Acting Injectable Agent, Paliperidone Palmitate. Poster No. 4-072 at the 161st Meeting of the American Psychiatric Association (APA), Washington, DC, USA, May 3-8, 2008.

Kramer M, Litman R, Lane R, Lim P, Hough D, Palumbo J, Eerdekens M Efficacy and Tolerability of Two Fixed Dosages of Paliperidone Palmitate in the Treatment of Schizophrenia: Results of a 9-Week Placebo-Controlled Trial. Poster at the 20th US Psychiatric and Mental Health Congress (USPMHC), Orlando, Florida, USA, Oct. 11-14, 2007.

Pandina G, Lane R, Gopal S, Gassmann-Mayer C, Hough D, Remmerie B, Simpson G A Randomized, Double-Blind, Comparative Study of Flexible Doses of Paliperidone Palmitate and Risperidone Long-Acting Therapy in Patients with Schizophrenia. Poster at the 48th Annual Meeting of the American College Neuropsychopharmacology (ACNP), Hollywood, Florida, USA, Dec. 6-10, 2009.

Pandina GJ, Lindenmayer JP, Lull J, Lim P, Gopal S, Kusumakar V, Yuen E, Palumbo J A Randomized, Placebo-Controlled Study to Assess the Efficacy and Safety of Three Doses of Paliperidone Palmitate in Adults with an Acute Exacerbation of Schizophrenia. Poster at the 12th International Congress on Schizophrenia Research (ICOSR), San Diego, California, USA, Mar. 28-Apr. 1, 2009.

Pandina GJ, Lindenmayer JP, Lull J, Lim P, Gopal S, Kusumakar V, Yuen E, Palumbo J A Randomized, Placebo-Controlled Study to Assess the Efficacy and Safety of Three Doses of Paliperidone Palmitate in Adults with an Acute Exacerbation of Schizophrenia. Poster at the 12th Annual Meeting of the College of Psychiatric and Neurologic Pharmacists (CPNP), Jacksonville, Florida, Apr. 19-22, 2009.

Samtani MN, Gopal S, Kern Sliwa J, Haskins JT, Alphs L, Stuyckens K, Vermeulen A Management of Missed Paliperidone Palmitate Doses Based on Pharmacokinetic Modeling and Simulation. Poster at the 49th Annual Meeting of the New Clinical Drug Evaluation Unit (NCDEU) of the National Institute of Mental Health (NIMH), Hollywood, Florida, USA, Jun. 29-Jul. 2, 2009.

Samtani MN, Gopal S, Kern Sliwa J, Haskins JT, Alphs L, Stuyckens K, Vermeulen A, Switching to Paliperidone Palmitate From Other Antipsychotics: Guidance Based on Pharmacokinetic Modeling and Simulation, 49th Annual Meeting of the New Clinical Drug Evaluation Unit (NCDEU) of the National Institute of Mental Health (NIMH), Hollywood, Florida, USA, Jun. 29-Jul. 2, 2009, Proceedings/AbstractBook, p. 68, 2009.

Samtani MN, Gopal S, Kern Sliwa J, Haskins T, Alphs L, Stuyckens K, Vermeulen A Paliperidone Palmitate Dosing in Special Patient Populations Including the Elderly and Those With Renal Impairment or Differing Body Mass Index: Guidance Based on Pharmacokinetic Modeling and Simulation. Poster at the American Conference on Pharmacometrics, Mashantucket, Connecticut, USA, Oct. 4-7, 2009.

Samtani MN, Haskins JT, Alphs L, Sliwa JK, Stuyckens K, Herben V, Vermeulen A Maintenance Dosing of Once-Monthly (4-Weekly) Paliperidone Palmitate in Schizophrenia: Pharmacokinetic Rationale Based on Population Simulations. Poster No. 21 at the 12th Annual Meeting of the College of Psychiatric and Neurologic Pharmacists (CPNP), Jacksonville, Florida, Apr. 19-22, 2009.

Samtani MN, Haskins JT, Gopal S, Sliwa JK, Alphs L, Stuyckens K, Vermeulen A Dosing Information for Paliperidone Palmitate—A Once-Monthly Injectable Atypical Antipsychotic—Based on Population Pharmacokinetic Analysis. Poster No. 310 at the 22nd US Psychiatric and Mental Health Congress (USPMHC), Las Vegas, Nevada, USA, Nov. 2-5, 2009.

Samtani MN, Sliwa JK, Haskins JT, Alphs L, Stuyckens K, Herben V, Vermeulen A Initiation Dosing of Deltoid Intramuscular Paliperidone Palmitate in Schizophrenia: Pharmacokinetic Rationale Based on Modeling and Simulation. Poster No. 19 at the 12th Annual Meeting of the College of Psychiatric and Neurologic Pharmacists (CPNP), Jacksonville, Florida, Apr. 19-22, 2009.

Samtani MN, Vermeulen A, Stuyckens K, Population Pharmacokinetics of Intramuscular Paliperidone Palmitate in Patients with Schizophrenia A Novel Once-Monthly, Long-Acting Formulation of an Atypical Antipsychotic, Clinical Pharmacokinetics 48 (9), p. 585-600, 2009.

Sikirica M, Crivera C, Dirani R, Cost-Effectiveness of Paliperidone Palmitate Versus Oral Atypicals in the US. Poster No. NR6-5 at the 163rd Annual Meeting of the American Psychiatric Association (APA), New Orleans, Louisiana, USA, May 22-26, 2010.

Turner N, Bossie CA, Haskins JT, Kern Sliwa J, Ma YW, Alphs L Effects of Paliperidone Palmitate in Acutely ill Subjects With a Marked to Severe Exacerbation of Schizophrenia. Poster No. NR6-26 at the 163rd Annual Meeting of the American Psychiatric Association (APA), New Orleans, Louisiana, USA, May 22-26, 2010.

Alphs et al., "Are the Long-Acting Intramuscular Formulations of Risperidone or Paliperidone Palmitate Associated with Post-Injection Delirium/Sedation Syndrome? An Assessment of Safety Databases", Current Drug Safety, 2011, 6, 43-45.

Alphs et al., "Paliperidone Palmitate Versus Risperidone Long-Acting Therapy in Markedly to Severely ill Subjects With Schizophrenia", Poster presented at the 23rd Annual US Psychiatric and Mental Health Congress; Supported by Ortho-McNeil Janssen Scientific Affairs, LLC Nov. 18-21, 2010; Orlando, FL, USA.

Alphs et al., "Tolerability of Paliperidone Palmitate Initiation Doses in Subjects with Recently Diagnosed Schizophrenia", Poster handout presented at The Scientific Program of XXVII CINP Congress, Hong Kong. Jun. 6-10, 2010.

Alphs et al., "Tolerability of Paliperidone Palmitate Initiation Doses in Subjects with Recently Diagnosed Schizophrenia", Poster presented at The Scientific Program of XXVII CINP Congress, Hong Kong. Jun. 6-10, 2010.

Cleton et al., Clinical Pharmacology & Therapeutics, Mosby-Year Book, St. Louis, MO, US, vol. 81, No. Suppl. 1, p. S63 (2007).

Cockcroft et al., Prediction of creatinine clearance from serum creatinine, Nephron, 16:31-41, 1976.

Fleischhacker, W. Wolfgang et al., "A randomized trial of paliperidone palmitate and risperidone long-acting injectable in schizophrenia", International Journal of Neuropsychopharmacology, pp. 1-12, CINP 2011.

(56) References Cited

OTHER PUBLICATIONS

Gopal et al., "A 52-week open-label study of the safety and tolerability of paliperidone palmitate in patients with schizophrenia", J Psychopharmacol. 2010; First View: 1-13.
Gopal et al., "Dosing Information for Paliperidone Palmitate—A Once-Monthly Injectable Atypical Antipsychotic—Based on Population Pharmacokinetic Analysis", Poster presented at The Scientific Program of XXVII CINP Congress, Hong Kong. Jun. 6-10, 2010.
Gopal et al., "Efficacy and safety of paliperidone palmitate in adult patients with acutely symptomatic schizophrenia: a randomized, double-blind, placebo-controlled, dose-response study", International Clinical Psychopharmacology 2010, vol. 25 No. 5, pp. 247-256.
Gopal et al., Risk of Cardiovascular Morbidity and Sudden Death with Risperidone and Paliperidone Treatment: Analysis of 64 Randomized, Double-Blind Trials, NR 10-24 Presented at the 164th Annual Meeting—American Psychiatric Association, May 14-18, 2011; Honolulu, Hawaii.
Hough et al., "Paliperidone palmitate maintenance treatment in delaying the time-to-relapse in patients with schizophrenia: A randomized, double-blind, placebo-controlled study", Schizophrenia Research 116 (2010) 107-117.
Hough et al., "Safety and tolerability of deltoid and gluteal injections of paliperidone palmitate in schizophrenia", Prog Neuropsychopharmacol Biol Psychiatry. 2009;33:1022-1031.
Li et al., "A Comparative Randomized, Open-label, Rater-blinded Study of Paliperidone Palmitate and Risperidone Long-Acting Injectable Therapy in Patients with Schizophrenia", Poster No. P-11-005 presented at the XXVII CINP Congress, Jun. 6-10, 2010; Hong Kong.
Nasrallah et al., "A Controlled, Evidence-Based Trial of Paliperidone Palmitate, A Long-Acting Injectable Antipsychotic, in Schizophrenia", Neuropsychopharmacology (2010) 35, 2072-2082.
Pandina et al., "A double-blind study of paliperidone palmitate and risperidone long-acting injectable in adults with schizophrenia", Progress in Neuro-Psychopharmacology & Biological Psychiatry 2011;35:218-226.
Pandina et al., "A randomized, placebo-controlled study to assess the efficacy and safety of 3 doses of paliperidone palmitate in adults with acutely exacerbated schizophrenia", J Clin Psychopharmacol. 2010;30:235-244.
Revill et al., Drugs of the Future, Prous Science, ES, vol. 31, No. 7, pp. 579-584 (2006).
Samtani et al., "Dosing and Switching Strategies for Paliperidone Palmitate", CNS Drugs 2011; 25(10): 829-845.
Samtani et al., "Expansion of Paliperidone Palmitate Day 8 Dose Window from ± 2 Days to ± 4 Days: Model-Based Pharmacokinetic Simulation and Safety Data", Poster presented at the 24th Annual U.S. Psychiatric and Mental Health Congress Meeting, Nov. 7-10, 2011, Las Vegas, Nevada.
Samtani et al., "Expansion of Paliperidone Palmitate Day 8 Dose Window from ± 2 Days to ± 4 Days: Model-Based Pharmacokinetic Simulation and Safety Data", Poster handout presented at the 24th Annual U.S. Psychiatric and Mental Health Congress Meeting, Nov. 7-10, 2011, Las Vegas, Nevada.
Samtani et al., "Switching to Paliperidone Palmitate[1,2] from Other Depot Antipsychotics Guidance Based on Pharmacokinetic Simulations", Population Approach Group in Europe, Applications—CNS (Group IV) Abstr 1839, Berlin, Germany. Jun. 8-11, 2010.
Samtani, Mahesh N., "Use of Model Based Simulations to Support the Paliperidone Palmitate Label", AAPS Workshop on Facilitating Oral Product Development and Reducing Regulatory Burden through Novel Approaches to Assess Bioavailability/Bioequivalence, Oct. 22-23, 2011, Washington.
Sheehan et al., "The Management of Antipsychotic Treatment Discontinuation and Interruptions Using Model-Based Simulations", Poster presented at the 51st Annual NCDEU New Research Approaches for Mental Health Interventions Meeting, Jun. 13-16, 2011, Boca Raton, Florida.
Sliwa et al., "Tolerability and Efficacy of Paliperidone Palmitate vs Risperidone Long-acting Injection in Subjects with Recently Diagnosed Schizophrenia", Presented at the 13th International Congress on Schizophrenia Research; Apr. 2-6, 2011; Colorado Springs, Colorado, USA.
Alen et al., Ansel's Pharmaceutical Dosage Forms and Drug Delivery Systems, $8^{th}$ Edition, 2005; pp. 260-263, 652-653, 682.
Guidance Document: Patented Medicines (Notice of Compliance) Regulations, Health Canada, Nov. 12, 2010.
New Drug Application (NDA) dated Oct. 25, 2007 submitted under section 505(b) of the Federal Food, Drug, and Cosmetic Act for Invega Sustenna (paliperidone palmitate) 39mg, 78mg, 117mg, 156mg, and 234 mg extended-release injectable suspension, date of letter is Jul. 31, 2009.
Supplemental New Drug Application (sNDA) dated Mar. 14, 2011, submitted under section 505(b) of the Federal Food, Drug, and Cosmetic Act (FDCA) for Invega Sustenna (paliperidone palmitate) extended-release injectable suspension, 39 mg, 78 mg, 117 mg, 156 mg, and 234 mg.
Alphs et al. Annals of General Psychiatry 2011, 10:12.
Altamura et al., Intramuscular preparations of antipsychotics: uses and relevance in clinical practice. Drugs. 2003; 63(5): 493-512.
Berwaerts et al., Journal of Affective Disorders 138 (2012) 247-258.
Canuso et al. 2010, Expert Opinion Pharmacother., vol. 11 (15), pp. 2557-2567.
Cleton et al., Assessment of the Dose Proportionality of Paliperidone Palmitate 25, 50, 100 and 150 MG EQ., A New Long-Acting Injectable Antipsychotic Following Administration in the Deltoid or Gluteal Muscles, PI-74, Clinical Pharmacology & Therapeutics, vol. 83, Supplement 1, Mar. 2008, S31.
Ereshefsky L., Pharmacokinetics and drug interactions: update for new antipsychotics. J Clin Psychiatry. 1996;57 Suppl 11:12-25.
Gefvert et al. Pharmacokinetics and D2 receptor occupancy of long-acting injectable risperidone (Risperdal Consta) in patients with schizophrenia. Int J Neuropsychopharmacol. 2005; 8(1): 27-36.
Kane et al., Guidelines for depot antipsychotic treatment in schizophrenia. European Neuropsychopharmacology Consensus Conference in Siena, Italy. Eur Neuropsychopharmacol. 1998; 8(1): 55-66.
Levron et al., Clinical pharmacokinetics of haloperidol decanoate. Comparison with other prolonged-action neuroleptics. Encephale. 1987; 13(2): 83-7 [see English Summary as provided].
Markowitz et al., "Benefit-Risk Assessment of Maintenance Therapy in Schizophrenia Comparing Long-Acting Injectable (LAI) Paliperidone Palmitate with Paliperidone ER", Presented at the 164th Annual Meeting of the American Psychiatric Association, May 14-18, 2011, Honolulu, HI, USA.
Mauri et al., Clinical pharmacokinetics of atypical antipsychotics: a critical review of the relationship between plasma concentrations and clinical response. Clin Pharmacokinet. 2007;46(5):359-88.
Pandina et al., Progress in Neuro-Psychopharmacology & Biological Psychiatry 35 (2011) 218-226.
Sheehan et al., Comparison of the Peak-to-trough Fluctuation in Plasma Concentration of Long-acting Injectable Antipsychotics and Their Oral Equivalents, Innov Clin Neurosci. 2012;9(7-8):17-23.
Vermeir et al., Absorption, metabolism, and excretion of paliperidone, a new monoaminergic antagonist, in humans. Drug Metab Dispos. Apr. 2008;36(4):769-79.
Lewyn-Briscoe et al., U.S. Appl. No. 13/903,638.
International Search Report Re: International Application No. PCT/US2010/054807 dated Jan. 11, 2011.
Office Action mailed Feb. 28, 2013 in U.S. Appl. No. 12/916,910.
Kazuo Yamada et al., Future Potentiality of Pharmacotherapy for Schizophrenia in Acute Phase, Clinical Psychopharmacology, vo. 8, No. 10 (2005), pp. 1563-1568.
Takashi Yoshio, Sustained-release Antipsychotic Drugs (depot drugs), Psychiatric Nursing, vol. 33, No. 4 (2006), pp. 64-67.
Gibaldi's Drug Delivery Systems in Pharmaceutical Care. edited by Mary Lee, Archana Desai, American Society of Health-System Pharmacists, Inc. (2007), pp. 103-108.
Third Party Observations filed during prosecution of corresponding EP Appl No. 08863534.7.

(56) References Cited

OTHER PUBLICATIONS

Australian Patent Opposition for AU Patent Appl No. 2008340101 dated May 20, 2015.
Statement of Grounds and Particulars dated Aug. 19, 2015 re: Australian Patent Opposition for AU Patent Appl No. 2008340101.
Cleton A, Rossenu S, Crauwels H, et al. A single-dose, open-label, parallel, randomized, dose-proportionality study of paliperidone after intramuscular injections of paliperidone palmitate in the deltoid or gluteal muscle in patients with schizophrenia. *J Clin Pharmacol.* 2014;54(9):1048-1057.
Cleton A, Rossenu S, Hough D, Crauwels H, Vandebosch A, Berwaerts J, Eerdekens M, Francetic, I. "Evaluation of the pharmacokinetic profile of gluteal versus deltoid intramuscular Injections of paliperidone palmitate 100 mg equivalent in patients with schizophrenia" *Clin.Pharmacal. Therapeutics.* Published Mar. 2008.
Cockshott WP, Thompson GT, Howlett LJ, Seeley ET. Intramuscular or intralipomatous injections? *N Engl J Med.* 1982;307(6):356-358.
Haramati N, Lorans R, Lutwin M, Kaleya RN. Injection granulomas. Intramuscle or intrafat? *Arch Fam Med.* 1994;3(2):146-148.
Janicak, P. G. and Winans, E. A. "Paliperidone ER: a review of the clinical trial data" *Neuropsychiatr. Dis. Treat.* Dec. 3, 2007(6): 869-897 Published Jan. 15, 2008.
Rosen, H, and Abribat, T. "The rise and rise of drug delivery" *Nat. Rev. Drug Discov.* May 4, 2005(5): 381-5.
Rossenu S, Cleton A, Hough D, et al. Pharmacokinetic profile after multiple deltoid or gluteal intramuscular injections of paliperidone palmitate in patients with schizophrenia. *Clinical Pharmacology in Drug Development.* 2015;4(4):270-278.
Samtani MN, Vermeulen A, Stuyckens K. Population pharmacokinetics of intramuscular paliperidone palmitate in patients with schizophrenia: a novel once-monthly, long-acting formulation of an atypical antipsychotic. *Clin Pharmacokinet.* 2009;48(9):585-600.
Synopsis of the Phase III clinical study described at Example 8 of the opposed application accessed at http://yoda.yale.edu/sites/default/files/nct00590577.pdf on Aug. 17, 2015, Issue Date: Sep. 12, 2008.
Yin J, Collier AC, Barr AM, Honer WG, Procyshyn RM. Paliperidone Palmitate Long-Acting Injectable Given Intramuscularly in the Deltoid Versus the Gluteal Muscle: Are They Therapeutically Equivalent? *J Clin Psychopharmacol.* 2015;35(4):447-449.
Kreyenbuhi, et al., "Adding or Switching Antipsychotic Medications in Treatment-Refractory Schizophrenia", Psychiatr Serv., Jul. 2007, pp. 983-990, vol. 58(7).
Third Party Observations dated Jan. 28, 2016 filed during prosecution of EP Application No. 10773821.3.
Office Action mailed Mar. 24, 2015 in U.S. Appl. No. 13/903,638.
Final Office Action mailed Oct. 22, 2015 in U.S. Appl. No. 13/903,638.
Cirincione, et al., "Population pharmacokinetics of paliperidone ER in healthy subjects and patients with schizophrenia", clinical Pharmacology & Therapeutics, vol. 81, Issue Supplement SI, P. S19 (published in Mar. 2007).

DOSING REGIMEN ASSOCIATED WITH LONG ACTING INJECTABLE PALIPERIDONE ESTERS

CROSS REFERENCE TO RELATED APPLICATIONS

This application claims the benefit of U.S. Provisional Application 61/014,918, filed on Dec. 19, 2007 and U.S. Provisional Application 61/120,276, filed on Dec. 5, 2008.

FIELD OF THE INVENTION

This invention relates to a method of treating patients in need of treatment with long acting injectable paliperidone palmitate formulations.

BACKGROUND OF THE INVENTION

Antipsychotic medications are the mainstay in the treatment of schizophrenia, schizoaffective disorder, and schizophreniform disorders. Conventional antipsychotics were introduced in the mid-1950s. These typical or first generation drugs are usually effective in controlling the positive symptoms of schizophrenia, but are less effective in moderating the negative symptoms or the cognitive impairment associated with the disease. Atypical antipsychotics or second generation drugs, typified by risperidone and olanzapine, were developed in the 1990s, and are generally characterized by effectiveness against both the positive and negative symptoms associated with schizophrenia.

Paliperidone palmitate is the palmitate ester of paliperidone (9-hydroxy-risperidone), a monoaminergic antagonist that exhibits the characteristic dopamine $D_2$ and serotonin (5-hydroxytryptamine type 2A) antagonism of the second-generation, atypical antipsychotic drugs. Paliperidone is the major active metabolite of risperidone. Extended release (ER) osmotic controlled release oral delivery (OROS) paliperidone, as a tablet formulation, is marketed in the United States (U.S.) for the treatment of schizophrenia and maintenance of effect.

Paliperidone palmitate is being developed as a long-acting, intramuscular (i.m.), injectable aqueous nanosuspension for the treatment of schizophrenia and other diseases that are normally treated with antipsychotic mediations. Because of extreme low water solubility, paliperidone esters such as paliperidone palmitate dissolve slowly after an i.m. injection before being hydrolyzed to paliperidone and made available in the systemic circulation.

Many patients with these mental illnesses achieve symptom stability with available oral antipsychotic medications; however, it is estimated that up to 75% have difficulty adhering to a daily oral treatment regimen, i.e. compliance problems. Problems with adherence often result in worsening of symptoms, suboptimal treatment response, frequent relapses and re-hospitalizations, and an inability to benefit from rehabilitative and psychosocial therapies.

Paliperidone palmitate injection has been developed to provide sustained plasma concentrations of paliperidone when administered once monthly, which may greatly enhance compliance with dosing. Paliperidone palmitate was formulated as an aqueous nano suspension as is described in U.S. Pat. Nos. 6,577,545 and 6,555,544. However, after the data was analyzed from the clinical trials of this formulation it was discovered that the absorption of paliperidone from these injections was far more complex than was originally anticipated. Additionally, attaining a potential therapeutic plasma level of paliperidone in patients was discovered to be dependent on the site of injection until steady state concentration is reached. Due to the challenging nature of ensuring an optimum plasma concentration-time profile for treating patients with paliperidone it is desirable to develop a dosing regimen that fulfills this goal in patients in need of treatment.

SUMMARY OF THE INVENTION

In one embodiment of the present invention there is provided a dosing regimen for administering paliperidone esters to a psychiatric patient in need of treatment comprising administering intramuscularly in the deltoid a first loading dose from about 100 mg-eq. to about 150 mg-eq. of paliperidone as a paliperidone palmitate formulated in a sustained release formulation on the first day of treatment; administering intramuscularly a second loading dose from about 100 mg to about 150 mg-eq of paliperidone as a paliperidone palmitate formulated in a sustained release formulation between about the 6th to 10th day of treatment; and administering intramuscularly in the gluteal a maintenance dose of about 25 to about 150 mg-eq. of paliperidone as a paliperidone ester in a sustained release formulation on between about the $34^{th}$ and about the 38th day of treatment.

In one embodiment of the present invention there is provided a dosing regimen for administering paliperidone esters to a psychiatric patient in need of treatment comprising administering intramuscularly in the deltoid a first loading dose from about 100 mg-eq. to about 150 mg-eq. of paliperidone as a paliperidone palmitate formulated in a sustained release formulation on the first day of treatment; administering intramuscularly a second loading dose from about 100 mg to about 150 mg-eq of paliperidone as a paliperidone palmitate formulated in a sustained release formulation between about the 6th to 10th day of treatment; and administering intramuscularly in the gluteal a maintenance dose of about 25 to about 150 mg-eq. of paliperidone as a paliperidone ester in a sustained release formulation approximately monthly from the date of the second loading dose.

In another embodiment of the present invention there is provided a dosing regimen for administering paliperidone palmitate to a psychiatric patient in need of treatment comprising administering intramuscularly in the deltoid of a patient in need of treatment a first loading dose from about 100 mg-eq. to about 150 mg-eq of paliperidone as paliperidone palmitate formulated in a sustained release formulation on the first day of treatment; administering intramuscularly in the deltoid muscle of the patient in need of treatment a second loading dose from about 100 mg-eq. to about 150 mg-eq. of paliperidone as paliperidone palmitate formulated in a sustained release formulation on the eighth day of treatment; and administering intramuscularly in the deltoid or gluteal muscle of the patient in need of treatment a maintenance dose of about 25 mg-eq. to about 75 mg-eq. of paliperidone as paliperidone palmitate in a sustained release formulation on between about the 34th day and the 38th day of treatment.

In another embodiment of the present invention there is provided a dosing regimen for administering paliperidone palmitate to a psychiatric patient in need of treatment comprising administering intramuscularly in the deltoid of a patient in need of treatment a first loading dose of about 150 mg-eq of paliperidone as paliperidone palmitate formulated in a sustained release formulation on the first day of treatment; administering intramuscularly in the deltoid muscle of the patient in need of treatment a second loading dose from about 100 mg-eq. of paliperidone as paliperidone palmitate formulated in a sustained release formulation on the eighth day of treatment; and administering intramuscularly in the deltoid or gluteal muscle of the patient in need of treatment a maintenance dose of about 25 mg-eq. to about 75 mg-eq. of paliperidone as paliperidone palmitate in a sustained release formulation approximately monthly from the date of the second loading dose.

In another embodiment of the present invention there is provided a dosing regimen for administering paliperidone palmitate to a psychiatric patient in need of treatment comprising administering intramuscularly in the deltoid of a patient in need of treatment a first loading dose of about 150 mg-eq of paliperidone as paliperidone palmitate formulated in a sustained release formulation on the first day of treatment; administering intramuscularly in the deltoid muscle of the patient in need of treatment a second loading dose from about 100 mg-eq. of paliperidone as paliperidone palmitate formulated in a sustained release formulation on the eighth day of treatment; and administering intramuscularly in the deltoid or gluteal muscle of the patient in need of treatment a maintenance dose of about 75 mg-eq. of paliperidone as paliperidone palmitate in a sustained release formulation approximately monthly from the date of the second loading dose.

In yet another embodiment of the present invention there is provided a dosing regimen for administering paliperidone esters to a renally impaired psychiatric patient in need of treatment comprising administering intramuscularly in the deltoid a first loading dose of about 75 mg-eq of paliperidone as a paliperidone palmitate formulated in a sustained release formulation on the first day of treatment; administering intramuscularly a second loading dose of about 75 mg-eq of paliperidone as a paliperidone palmitate formulated in a sustained release formulation between about the 6th to 10th day of treatment; and administering intramuscularly in the gluteal a maintenance dose of about 25 mg-eq. to about 75 mg-eq of paliperidone as a paliperidone palmitate in a sustained release formulation on between about the $34^{th}$ and about the 38th day of treatment.

In yet another embodiment of the present invention there is provided a dosing regimen for administering paliperidone esters to a renally impaired psychiatric patient in need of treatment comprising administering intramuscularly in the deltoid a first loading dose of about 100 mg-eq of paliperidone as a paliperidone palmitate formulated in a sustained release formulation on the first day of treatment; administering intramuscularly a second loading dose of about 75 mg-eq of paliperidone as a paliperidone palmitate formulated in a sustained release formulation between about the 6th to 10th day of treatment; and administering intramuscularly in the gluteal a maintenance dose of about 25 mg-eq. to about 75 mg-eq of paliperidone as a paliperidone palmitate in a sustained release formulation approximately monthly from the date of the second loading dose.

In a further embodiment of the present invention there is provided a dosing regimen for administering paliperidone palmitate to a psychiatric patient in need of treatment comprising administering intramuscularly in the deltoid of a patient in need of treatment a first loading dose of about 75 mg-eq. of paliperidone as paliperidone palmitate formulated in a sustained release formulation on the first day of treatment; administering intramuscularly in the deltoid muscle of the patient in need of treatment a second loading dose of about 75 mg-eq of paliperidone as paliperidone palmitate formulated in a sustained release formulation on the eighth day of treatment; and administering intramuscularly in the deltoid or gluteal muscle of the patient in need of treatment a maintenance dose of from about 25 mg-eq. to about 50 mg-eq. of paliperidone as paliperidone palmitate in a sustained release formulation on about the 34th day and the 38th day of treatment.

In one embodiment of the present invention there is provided a dosing regimen for administering paliperidone esters to a psychiatric patient in need of treatment comprising administering intramuscularly in the deltoid a first loading dose of about 150 mg-eq. of paliperidone as a paliperidone palmitate formulated in a sustained release formulation on the first day of treatment; thereafter administering intramuscularly a second maintenance dose of from about 25 mg-eq. to about 100 mg-eq of paliperidone as a paliperidone palmitate formulated in a sustained release formulation between about the 6th to 10th day of treatment; and administering intramuscularly in the gluteal a maintenance dose of about 25 to about 100 mg-eq. of paliperidone as a paliperidone palmitate in a sustained release formulation on between about the $34^{th}$ and about the 38th day of treatment.

In a further embodiment of the present invention there is provided a dosing regimen for administering paliperidone palmitate to a psychiatric patient in need of treatment comprising administering intramuscularly in the deltoid of a patient in need of treatment a first loading dose from about 150 mg-eq. of paliperidone as a paliperidone palmitate ester in a sustained release formulation on the first day of treatment; thereafter administering intramuscularly in the deltoid muscle of the patient in need of treatment a maintenance dose from about 25 mg-eq. to about 100 mg-eq. of paliperidone as paliperidone palmitate formulated in a sustained release formulation on the eighth day of treatment; and administering intramuscularly in the deltoid or gluteal muscle of the patient in need of treatment a maintenance dose of about 25 mg-eq. to about 100 mg-eq. of paliperidone as paliperidone palmitate in a sustained release formulation on about the 34th day and the 38th day of treatment.

This and other objects and advantages of the present invention may be appreciated from a review of the present applications.

DETAILED DESCRIPTION

Figure 1:
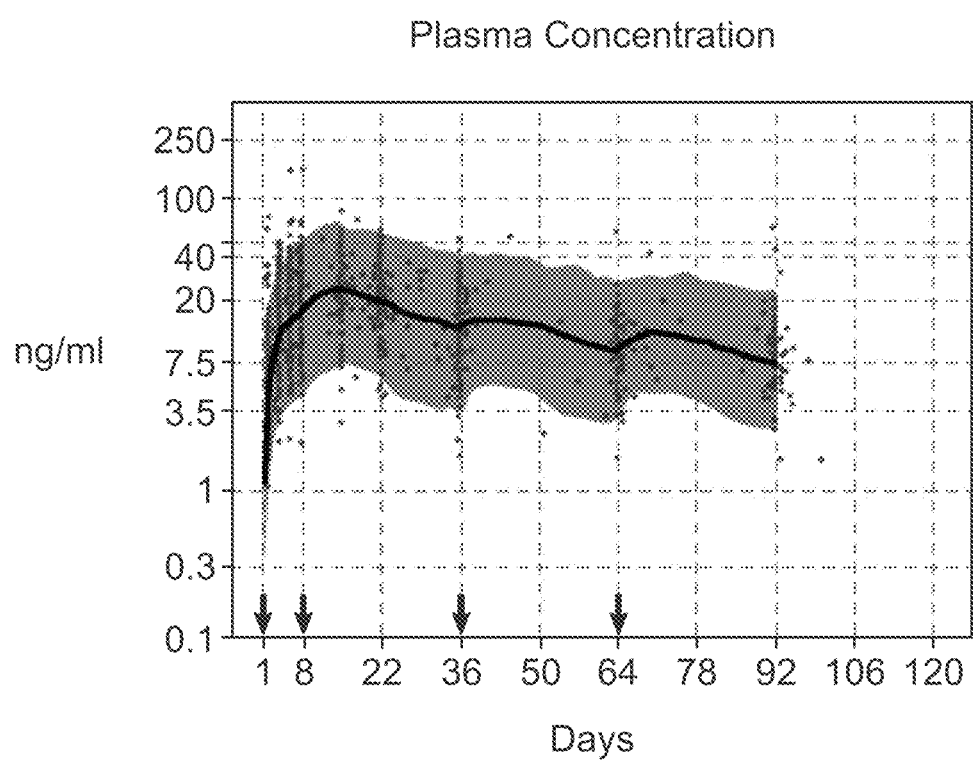
FIG. 1 shows the observed versus the population pharmacokinetics model simulation for plasma paliperidone concentrations for paliperidone palmitate 150 mg eq. in the deltoid on day 1, followed by 25 mg eq. in either the deltoid or gluteus on days 8, 36, and 64.

We have discovered after extensive analysis of the clinical data that paliperidone palmitate due to its dissolution rate-limited absorption exhibits flip-flop kinetics, where the apparent half-life is controlled by the absorption rate constant. Additionally the volume of injected drug product also impacts the apparent rate constant. It was also discovered that deltoid injections result in a faster rise in initial plasma concentration, facilitating a rapid attainment of potential therapeutic concentrations. Consequently, to facilitate patients' attaining a rapid therapeutic concentration of paliperidone it is preferred to provide the initial loading dose of paliperidone palmitate in the deltoids. The loading dose should be from about 100 mg-eq. to about 150 mg-eq. of paliperidone provided in the form of paliperidone palmitate. After the first or more preferably after the second loading dose injection patients will be approaching a steady state concentration of paliperidone in their plasma and may be injected in either the deltoid or the gluteal muscle thereafter. However, it is preferred that the patients receive further injections in the gluteal muscle.

In view of these discoveries the recommended dosing regimen for patients to attain a therapeutic plasma level of paliperidone is for patients to receive the first dose of paliperidone palmitate on day 1 of treatment, followed by a second dose between days 6 to 10 of treatment, then a third dose between days 34 to 38 of treatment or monthly ±7 days after the second dose. More preferably the patients will be administered a first dose on day 1, a second dose on day 8 and a third dose on or about day 36 of treatment or approximately monthly ±3 days after the second dose. The first two doses will preferably be injected in the deltoid muscle. Thereafter paliperidone palmitate will be administered by injection approximately once a month (e.g. monthly ±7 days or approximately once every four weeks) thereafter. To assure that a potential therapeutic plasma level of paliperidone is attained at least a first loading dose of 150 mg-eq of paliperidone as a paliperidone palmitate ester should be administered on day one of treatment. Preferably the first two doses will be loading dose of between from about 100 mg-eq. to about 150 mg-eq. of paliperidone as a paliperidone palmitate ester to assure that a potential therapeutic plasma level of paliperidone is attained by the patient. The subsequent doses thereafter will drop to a therapeutic maintenance dose of from about 25 mg-eq. to 150 mg-eq. per month (±7 days). Preferably the maintenance dose will be from about 25 mg eq. to about 100 mg eq; more preferably the maintenance dose will be from about 25 mg eq. to about 75 mg eq; and most preferably the maintenance dose initially will be about 50 mg eq., or more preferably the maintenance dose initially will be about 75 mg eq. which may be administered intramuscularly into the deltoid or gluteal muscle, but more preferably will be administered in the gluteal muscle. Those of ordinary skill in the art will understand that the maintenance dose may be titrated up or down in view of the patients condition (response to the medication and renal function).

Since paliperidone is mainly eliminated through the kidneys, patients with renal impairment will have a higher total exposure to paliperidone after i.m. injections of paliperidone palmitate. For patients with renal impairment it would desirable to adjust the loading doses to account for the increased exposure levels of patients with renal impairment. For patients with mild renal impairment the loading doses should be reduced to 75 mg-eq. for the first two loading doses. The maintenance doses should range from about 25 mg-eq. to about 75 mg-eq. and more preferably with range from about 25 mg-eq. to about 50 mg-eq. The doses would be administered on day 1 of treatment, followed by a second dose between days 6 to 10 of treatment, then a third dose between days 34 to 38 of treatment. More preferably patients will be administered a first dose on day 1, a second dose on day 8 and a third dose on day 36 of treatment. The first two doses will preferably be injected in the deltoid muscle. Thereafter paliperidone palmitate will be administered by injection approximately once a month (e.g. one a month ±7 days or once every four weeks) thereafter. For the purpose of this patent application renal function is estimated by glomerular filtration rate (GFR) usually measured by the creatinine clearance (best calculated from a 24-hour urine collection). Creatine clearance may be estimated by the Cockcroft and Gault method based on serum creatinine concentration, as described in Prediction of creatinine clearance from serum creatinine. Nephron 1976; vol 16. pages 31-41. Patients with mild renal impairment have a creatinine clearance of 50 to <80 mL/minute.

It is recommended that the second initiation dose of paliperidone palmitate be given about one week (6-10 days) after the first dose. To avoid a missed dose, patients may be given the second dose 2 days before or after the one-week time point. Similarly, the third and subsequent injections after the initiation regimen are recommended to be given monthly. To avoid a missed monthly dose, patients may be given the injection up to 7 days before or after the monthly time point.

After initiation, the recommended injection cycle of paliperidone palmitate is monthly. If less than 6 weeks have elapsed since the last injection, then the previously stabilized dose should be administered as soon as possible, followed by injections at monthly intervals.

If more than 6 weeks have elapsed since the last injection, reinitiation with the same dose the patient was previously stabilized to should be resumed in the following manner: 1) a deltoid injection as soon as practically possible, followed by 2) another deltoid injection one week later, and 3) resumption of either deltoid or gluteal dosing at monthly intervals.

If more than 6 months have elapsed since the last injection, it is recommended to re-initiate dosing as described above.

Additionally, in this patient population needle length and BMI index are two related variables that need to be considered to assure patients attain therapeutic concentration of paliperidone in the desired time frame. Patients with high BMI had lower plasma concentration of paliperidone and a lessened treatment response. The lower initial plasma concentration in high BMI patients was likely due to unintended partial or complete injection into adipose tissue, instead of deep injection into muscle. However, once steady-state plasma concentration are attained BMI no longer influenced plasma concentrations or clinical efficacy. From these observations it was determined that for patients weighing <90 kg (<200 lb) a 1-inch needle will be of adequate length to use in injections to reach the muscle tissue for deltoid injections with preferably a 23 gauge needle. However, for patients with high BMIs, ≥90 kg (≥200 lb) a 1.5-inch needle should be used for deltoid injections. For gluteal muscle injections a 1.5-inch needle should be used. Preferably the 1.5-inch needle will be a 22-gauge needle.

Paliperidone esters are psychotic agents belonging to the chemical class of benzisoxazole derivatives, which contains a racemic mixture of (+)- and (−)-paliperidone, which are described in U.S. Pat. No. 5,254,556 (incorporated herein by reference). The chemical name for paliperidone palmitate is (±)-3-[2-[4-(6-fluoro-1,2-benzisoxazol-3-yl)-1-piperidinyl] ethyl]-6,7,8,9-tetrahydro-2-methyl-4-oxo-4H-pyrido[1,2-α] pyrimidin-9-yl hexadecanoate. The structural formula is:

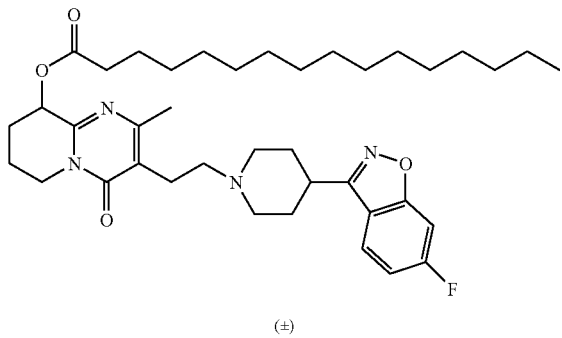 [SMILES: CCCCCCCCCCCCCCCC(=O)OC1CCCn2c1nc(C)c(CCN1CCC(c3noc4cc(F)ccc34)CC1)c2=O]

(±)

Paliperidone esters may be formulated with pharmaceutical excipients into injectable dosage forms as described in U.S. Pat. No. 5,254,556 and U.S. Pat. No. 6,077,843 (incorporated herein by reference). Injectable formulations may be formulated in aqueous carriers.

Currently it is preferred to administer paliperidone palmitate in a once monthly aqueous depot. Suitable aqueous depot formulations are described in U.S. Pat. No. 6,077,843 (incorporated herein by reference). The aqueous formulation would preferably be a nano particle suspension of wherein the nano particles would be of an averages size of less than 2000 nm to about 100 nm. Preferably the nano particles would have an average particle size (d50) of from about 1600 nm to 400 nm and most preferably about 1400 nm to 900 nm. Preferably the d90 will be less than about 5000 nm and more preferably less than about 4400 nm. As used herein, an effective average particle size (d50) of less than 2,000 nm means that at least 50% of the particles have a diameter of less than 2,000 nm when measured by art-known conventional techniques, such as sedimentation field flow fractionation, photon correlation spectroscopy or disk centrifugation. With reference to the effective average particle size, it is preferred that at least 90%, e.g. 5,000 nm. Most preferably, 90% of the particles have a size of less than 4,400 nm.

Suitable aqueous nano particle depot formulations are described in U.S. Pat. No. 6,555,544 (incorporated herein by reference). In one embodiment of the present invention the formulation would comprise nanoparticles, a surfactant, a suspending agent, and optionally one or more additional ingredients selected from the group consisting of preservatives, buffers and an isotonizing agents.

Useful surface modifiers are believed to include those that physically adhere to the surface of the active agent but do not chemically bond thereto.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENS™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phtalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol; poloxamers, such as PLURONIC™. F68, F108 and F127 which are block copolymers of ethylene oxide and propylene oxide available from BASF; poloxamines, such as TETRONIC™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; DUPONOL™ P which is a sodium lauryl sulfate available from DuPont; TRITON™ X-200 which is an alkyl aryl polyether sulfonate available from Rohm and Haas; TWEEN™. 20, 40, 60 and 80 which are polyoxyethylene sorbitan fatty acid esters available from ICI Specialty Chemicals; SPAN™ 20, 40, 60 and 80 which are sorbitan esters of fatty acids; ARLACEL™ 20, 40, 60 and 80 which are sorbitan esters of fatty acids available from Hercules, Inc.; CARBOWAX™ 3550 and 934 which are polyethylene glycols available from Union Carbide; CRODESTA™ F110 which is a mixture of sucrose stearate and sucrose distearate available from Croda Inc.; CRODESTA™ SL-40 which is available from Croda, Inc.; hexyldecyl trimethyl ammonium chloride (CTAC); bovine serum albumin and SA90HCO which is $C_{18}H_{17}CH_2(CON(CH_3)CH_2(CHOH)_4CH_2OH)_2$. The surface modifiers which have been found to be particularly useful include tyloxapol and a poloxamer, preferably, Pluronic™ F108 and Pluronic™ F68.

Pluronic™ F108 corresponds to poloxamer 338 and is the polyoxyethylene, polyoxypropylene block copolymer that conforms generally to the formula $HO[CH_2\ CH_2O]_x[CH(CH_3)CH_2O]_y[CH_2CH_2O]_z H$ in which the average values of x, y and z are respectively 128, 54 and 128. Other commercial names of poloxamer 338 are Hodag NONIONIC™ 1108-F available from Hodag, and SYNPERONIC™ PE/F108 available from ICI Americas.

The optimal relative amount of paliperidone palmitate and the surface modifier depends on various parameters. The optimal amount of the surface modifier can depend, for example, upon the particular surface modifier selected, the critical micelle concentration of the surface modifier if it forms micelles, the surface area of the antipsychotic agent, etc. The specific surface modifier preferably is present in an amount of 0.1 to 1 mg per square meter surface area of the paliperidone palmitate. It is preferred in the case of paliperidone palmitate (9-hydroxyrisperidone palmitate) to use PLURONIC™ F 108 as a surface modifier, a relative amount (w/w) of both ingredients of approximately 6:1 is preferred.

The particles of this invention can be prepared by a method comprising the steps of dispersing paliperidone palmitate in a liquid dispersion medium and applying mechanical means in the presence of grinding media to reduce the particle size of the antipsychotic agent to an effective average particle size of less than 2,000 nm. The particles can be reduced in size in the presence of a surface modifier. Alternatively, the particles can be contacted with a surface modifier after attrition.

A general procedure for preparing the particles of this invention includes (a) obtaining paliperidone palmitate in micronized form; (b) adding the micronized paliperidone palmitate to a liquid medium to form a premix; and (c) subjecting the premix to mechanical means in the presence of a grinding medium to reduce the effective average particle size.

The paliperidone palmitate in micronized form may be prepared using techniques known in the art. It is preferred that the particle size of the micronized paliperidone palmitate be less than about 100 µm as determined by sieve analysis. If the particle size of the micronized paliperidone palmitate is greater than about 100 µm, then it is preferred that the particles of paliperidone palmitate be reduced in size to less than 100 µm.

The micronized paliperidone palmitate can then be added to a liquid medium in which it is essentially insoluble to form a premix. The concentration of paliperidone palmitate in the liquid medium (weight by weight percentage) can vary widely and depends on the selected antipsychotic agent, the selected surface modifier and other factors. Suitable concentrations of paliperidone palmitate in compositions vary between 0.1 to 60%, preferably is from 0.5 to 30%, and more preferably, is approximately 7% (w/v). It is currently preferred to use a concentration of about 100 mg eq of paliperidone per ml or about 156 mg of paliperidone palmitate per ml.

A more preferred procedure involves the addition of a surface modifier to the premix prior to its subjection to mechanical means to reduce the effective average particle size. The concentration of the surface modifier (weight by weight percentage) can vary from 0.1% to 90%, preferably from 0.5% to 80%, and more preferably is approximately 7% (w/v).

The premix can be used directly by subjecting it to mechanical means to reduce the effective average particle size in the dispersion to less than 2,000 nm. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills—such as a sand mill and a bead mill. A media mill is preferred due to the relatively shorter milling time required to provide the desired reduction in particle size. For media milling, the apparent viscosity of the premix preferably is anywhere between 0.1 and 1 Pa·s. For ball milling, the apparent viscosity of the premix preferably is anywhere between 1 and 100 mPa·s.

The grinding media for the particle size reduction step can be selected from rigid media preferably spherical or particulate in form having an average size less than 3 mm and, more preferably, less than 1 mm. Such media desirably can provide the particles of the invention with shorter processing times and impart less wear to the milling equipment. The selection of the material for the grinding media is believed not to be critical. However, 95% ZrO stabilized with magnesia, zirconium silicate, and glass grinding media provide particles having levels of contamination which are acceptable for the preparation of pharmaceutical compositions. Further, other media, such as polymeric beads, stainless steel, titania, alumina and 95% ZrO stabilized with yttrium, are useful. Preferred grinding media have a density greater than 2.5 g/cm.sup.3 and include 95% ZrO stabilized with magnesia and polymeric beads.

The attrition time can vary widely and depends primarily upon the particular mechanical means and processing conditions selected. For rolling mills, processing times of up to two days or longer may be required.

The particles must be reduced in size at a temperature which does not significantly degrade the antipsychotic agent. Processing temperatures of less than 30° C. to 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, must be added to the dispersion after attrition in an amount as described for the premix above. Thereafter, the dispersion can be mixed by, for example, shaking vigorously. Optionally, the dispersion can be subjected to a sonication step using, for example, a ultrasonic power supply.

Aqueous compositions according to the present invention conveniently further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxy-propylene ethers. Preferably sodium carboxymethyl cellulose is used in a concentration of 0.5 to 2%, most preferably 1% (w/v). Suitable wetting agents for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of 0.5 to 3%, more preferably 0.5 to 2%, most preferably 1.1% (w/v).

Suitable buffering agents are salt of weak acids and should be used in amount sufficient to render the dispersion neutral to very slightly basic (up to pH 8.5), preferably in the pH range of 7 to 7.5. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-gamma-piccolinium chloride, phenylmercuric acetate and thimerosal. In particular, it is benzyl alcohol which can be used in a concentration up to 2% (w/v), preferably up to 1.5% (w/v).

Isotonizing agents are, for example, sodium chloride, dextrose, mannitol, sorbitol, lactose, sodium sulfate. The suspensions conveniently comprise from 0 to 10% (w/v)

isotonizing agent. Mannitol may be used in a concentration from 0 to 7% More preferably, however, from about 1 to about 3% (w/v), especially from about 1.5 to about 2% (w/v) of one or more electrolytes are used to render the suspension isotonic, apparently because ions help to prevent flocculation of the suspended ester. In particular, electrolytes of the buffer serve as isotonizing agent.

A particularly desirable feature for an injectable depot formulation relates to the ease with which it can be administered. In particular such an injection should be feasible using a needle as fine as possible in a span of time which is as short as possible. This can be accomplished with the aqueous suspensions of the present invention by keeping the viscosity below about 75 mPa·s, preferably below 60 mPa·s. Aqueous suspensions of such viscosity or lower can both easily be taken up in a syringe (e.g. from a vial), and injected through a fine needle (e.g a 21 G 1½ inch, 22 G 2 inch, 22 G 1¼ inch or 23 G 1 inch needle). The preferred needles for injection are 22 G 22 G 1½ inch regular wall and 23 G 1½ inch regular wall needles.

Ideally, aqueous suspensions according to the present invention will comprise as much prodrug as can be tolerated so as to keep the injected volume to a minimum, and as little of the other ingredients as possible. In particular, such a composition will comprise by weight based on the total volume of the composition: (a) from 3 to 20% (w/v) of the prodrug; (b) from 0.5 to 2% (w/v) of a wetting agent; (c) one or more buffering agents sufficient to render the composition neutral to very slightly basic (pH 8.5); (d) from 0.5 to 2% (w/v) of a suspending agent; (e) up to 2% (w/v) preservatives; and (f) water q.s. ad 100%. Preferably the aqueous suspension will be made under sterile conditions and no preservatives will be used. Appropriate methods to aseptically prepare paliperidone palmitate are described in WO 2006/114384 which is hereby incorporated by reference herein.

The preferred aqueous dosage form contains inactive ingredients that are polysorbate 20, polyethylene glycol 4000, citric acid monohydrate, disodium hydrogen phosphate anhydrous, sodium dihydrogen phosphate monohydrate, sodium hydroxide, and water for injection. The mg of compound delivered in such a dosage form to the patient may be from 25 to about 150 mg (e.g. 25 mg, 50 mg, 75 mg, 100 mg, 150 mg) injectable dosage form.

The term "psychiatric patient" as used herein, refers to a human, who has been the object of treatment, or experiment for a "mental disorder" and "mental illness" refer to those provided in the Diagnostic and Statistical Manual (DSM IV), American Psychological Association (APA). Those of ordinary skill in the art will appreciate that paliperidone esters (e.g. paliperidone palmitate), can be administered to psychiatric patients for all the known uses of risperidone. These mental disorders include, but are not limited to, schizophrenia; bipolar disorder or other disease states in which psychosis, aggressive behavior, anxiety or depression is evidenced. Schizophrenia refers to conditions characterized as schizophrenia, schizoaffective disorder and schizophreniform disorders, in DSM-IV-TR such as category 295.xx. Bipolar Disorder refers to a condition characterized as a Bipolar Disorder, in DSM-IV-TR such as category 296.xx including Bipolar I and Bipolar Disorder II. The DSM-IV-TR was prepared by the Task Force on Nomenclature and Statistics of the American Psychiatric Association, and provides clear descriptions of diagnostic categories. Pathologic psychological conditions, which are psychoses or may be associated with psychotic features include, but are not limited to the following disorders that have been characterized in the DSM-IV-TR. Diagnostic and Statistical Manual of Mental Disorders, Revised, 3rd Ed. (1994). The numbers in parenthesis refer to the DSM-IV-TR categories. The skilled artisan will recognize that there are alternative nomenclatures, nosologies, and classification systems for pathologic psychological conditions and that these systems evolve with medical scientific progress. Examples of pathologic psychological conditions which may be treated include, but are not limited to, Mild Mental Retardation (317), Moderate Mental Retardation (318.0), Severe Mental Retardation (318.1), Profound Mental Retardation (318.2), Mental Retardation Severity Unspecified (319), Autistic Disorders (299.00), Rett's Disorder (299.80), Childhood Disintegrative Disorders (299.10), Asperger's Disorder (299.80), Pervasive Developmental Disorder Not Otherwise Specified (299.80), Attention-Deficit/Hyperactivity Disorder Combined Type (314.01), Attention-Deficit/Hyperactivity Disorder Predominately Inattentive Type (314.00), Attention-Deficit/Hyperactivity Disorder Predominately Hyperactive-Impulsive Type (314.01), Attention-Deficit/Hyperactivity Disorder NOS (314.9), Conduct Disorder (Childhood-Onset and Adolescent Type 312.8), Oppositional Defiant Disorder (313.81), Disruptive Behavior Disorder Not Otherwise Specified (312.9), Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Alcohol Intoxication Delirium (291.0), Alcohol Withdrawal Delirium (291.0), Alcohol-Induced Persisting Dementia (291.2), Alcohol-Induced Psychotic Disorder with Delusions (291.5), Alcohol-Induced Psychotic Disorder with Hallucinations (291.3), Amphetamine or Similarly Acting Sympathomimetic Intoxication (292.89), Amphetamine or Similarly Acting Sympathomimetic Delirium (292.81), Amphetamine or Similarly Acting Sympathomimetic Induced Psychotic with Delusions (292.11), Amphetamine or Similarly Acting Sympathomimetic Induced Psychotic with Hallucinations (292.12), Cannabis-Induced Psychotic Disorder with Delusions (292.11), Cannabis-Induced Psychotic Disorder with Hallucinations (292.12), Cocaine Intoxication (292.89), Cocaine Intoxication Delirium (292.81), Cocaine-Induced Psychotic Disorder with Delusions (292.11), Cocaine-Induced Psychotic Disorder with Hallucinations (292.12), Hallucinogen Intoxication (292.89), Hallucinogen Intoxication Delirium (292.81), Hallucinogen-Induced Psychotic disorder with Delusions (292.11), Hallucinogen-Induced Psychotic disorder with Delusions (292.12), Hallucinogen-Induced Mood Disorder (292.84), Hallucinogen-Induced Anxiety Disorder (292.89), Hallucinogen-Related Disorder Not Otherwise Specified (292.9), Inhalant Intoxication (292.89), Inhalant Intoxication Delirium (292.81), Inhalant-Induced Persisting Dementia (292.82), Inhalant-Induced Psychotic Disorder with Delusions (292.11), Inhalant-Induced Psychotic with Hallucinations (292.12), Inhalant-Induced Mood Disorder (292.89), Inhalant-Induced Anxiety Disorder (292.89), Inhalant-Related Disorder Not Otherwise Specified (292.9), Opioid Intoxication Delirium (292.81), Opioid-Induced Psychotic Disorder with Delusions (292.11), Opioid Intoxication Delirium (292.81), Opioid-Induced Psychotic Disorder with Hallucinations (292.12), Opioid-Induced Mood Disorder (292.84), Phencyclidine (PCP) or Similarly Acting Arylcyclohexylamine Intoxication (292.89), Phencyclidine (PCP) or Similarly Acting Arylcyclohexylamine Intoxication Delirium (292.81), Phencyclidine (PCP) or Similarly Acting Arylcyclohexylamine Induced Psychotic Disorder with Delusions (292.11), Phencyclidine (PCP) or Similarly Acting Arylcyclohexylamine Induced Psychotic Disorder with Hallucinations (292.12), Phencyclidine (PCP) or Similarly Acting Arylcyclohexylamine Mood Disorder (292.84), Phencyclidine (PCP) or Similarly Acting Arylcyclohexylamine Induced Anxiety Disorder (292.89), Phencyclidine (PCP) or Similarly Acting Arylcyclohexylamine Related Disorder Not Otherwise Specified (292.9), Sedative, Hypnotic or Anxiolytic Intoxication (292.89), Sedation, Hypnotic or Anxiolytic Intoxication Delirium (292.81), Sedation, Hypnotic or Anxiolytic Withdrawal Delirium (292.81), Sedation, Hypnotic or Anxiolytic Induced Persisting Dementia (292.82), Sedation, Hypnotic or Anxiolytic-Induced Psychotic Disorder with Delusions (292.11), Sedation, Hypnotic or Anxiolytic-Induced Psychotic Disorder with Hallucinations (292.12), Sedation, Hypnotic or Anxiolytic-Induced Mood Disorder (292.84), Sedation, Hypnotic or Anxiolytic-Induced Anxiety Disorder (292.89), Other (or Unknown) Substance Intoxication (292.89), Other (or Unknown) Substance-Induced Delirium (292.81), Other (or Unknown) Substance-Induced Persisting Dementia (292.82), Other (or Unknown) Substance-Induced Psychotic Disorder with Delusions (292.11), Other (or Unknown) Substance-Induced Psychotic Disorder with Hallucinations (292.12), Other (or Unknown) Substance-Induced Mood Disorder (292.84), Other (or Unknown) Substance-Induced Anxiety Disorder (292.89), Other (or Unknown) Substance Disorder Not Otherwise Specified (292.9), Obsessive Compulsive Disorder (300.3), Post-traumatic Stress Disorder (309.81), Generalized Anxiety Disorder (300.02), Anxiety Disorder Not Otherwise Specified (300.00), Body Dysmorphic Disorder (300.7), Hypochondriasis (or Hypochondriacal Neurosis) (300.7), Somatization Disorder (300.81), Undifferentiated Somatoform Disorder (300.81), Somatoform Disorder Not Otherwise Specified (300.81), Intermittent Explosive Disorder (312.34), Kleptomania (312.32), Pathological Gambling (312.31), Pyromania (312.33), Trichotillomania (312.39), and Impulse Control Disorder NOS (312.30), Schizophrenia, Paranoid Type, (295.30), Schizophrenia, Disorganized (295.10), Schizophrenia, Catatonic Type, (295.20), Schizophrenia, Undifferentiated Type (295.90), Schizophrenia, Residual Type (295.60), Schizophreniform Disorder (295.40), Schizoaffective Disorder (295.70), Delusional Disorder (297.1), Brief Psychotic Disorder (298.8), Shared Psychotic Disorder (297.3), Psychotic Disorder Due to a General Medical Condition with Delusions (293.81), Psychotic Disorder Due to a General Medical Condition with Hallucinations (293.82), Psychotic Disorders Not Otherwise Specified (298.9), Major Depression, Single Episode, Severe, without Psychotic Features (296.23), Major Depression, Recurrent, Severe, without Psychotic Features (296.33), Bipolar Disorder, Mixed, Severe, without Psychotic Features (296.63), Bipolar Disorder, Mixed, Severe, with Psychotic Features (296.64), Bipolar Disorder, Manic, Severe, without Psychotic Features (296.43), Bipolar Disorder, Manic, Severe, with Psychotic Features (296.44), Bipolar Disorder, Depressed, Severe, without Psychotic Features (296.53), Bipolar Disorder, Depressed, Severe, with Psychotic Features (296.54), Bipolar II Disorder (296.89), Bipolar Disorder Not Otherwise Specified (296.80), Personality Disorders, Paranoid (301.0), Personality Disorders, Schizoid (301.20), Personality Disorders, Schizotypal (301.22), Personality Disorders, Antisocial (301.7), and Personality Disorders, Borderline (301.83).

The following non-limiting examples are provided to further illustrate the present invention.

The term "therapeutically effective amount" as used herein, means that amount of active compound or pharmaceutical agent that elicits the biological or medicinal response in human that is being sought by a researcher, medical doctor or other clinician, which includes alleviation of the symptoms of the disease or disorder being treated.

Those of skill in the treatment of diseases could easily determine the effective amount of paliperidone to administer for the treatment of the diseases listed above. In general it is contemplated that an effective amount of paliperidone for the treatment of mental disorders would be from about 0.01 mg/kg to about 2 mg/kg body weight. For the present invention it is preferred to dose patients with 25 mg-eq. to about 150 mg eq. paliperidone. The amount of paliperidone palmitate is provided in sufficient amount to provide the equivalent dose of paliperidone after the palmitic acid moiety is removed from the ester (e.g. 156 mg corresponds to paliperidone 100 mg). In one embodiment of present invention wherein paliperidone palmitate is administered by intramuscular injection once per month is preferred.

EXAMPLE 1

Paliperidone Palmitate Formulations a) Crystallization in Stainless Steel Reactor of 50 L All equipment was sterilized using dry heat sterilization.

A stainless steel reactor was charged with 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]-pyrimidin-4-one palmitate ester and ethanol parenteral grade (8 L/kg) and heated to reflux temperature (78-79° C.) while stirring. The product dissolved at about 70° C. The solution was filtered at 76° C. over a sterile 0.22 µm filter into a sterile crystallization reactor. The sterile filter was then washed with heated ethanol (1 L/kg).

The filtrate was reheated to reflux and then cooled to room temperature whereupon the product crystallized. The thus obtained suspension was reheated again. The solution was cooled using differing cooling gradients (in consecutive experiments, the mixture was reheated and cooled again; after each cooling gradient, a sample was taken and isolated using a filter. The crystals were dried in vacuo at 50° C. in Tyvek bags so as to prevent dust formation and the particle characteristics were determined.

Different batches were run, yielding product with a particle size distribution measured by laser diffraction as shown in Table 1.

TABLE 1

| | Crystallization | | | | | Particle size distribution | | |
|---|---|---|---|---|---|---|---|---|
| | Calculated cooling | | start at . . . | | start cooling | | | |
| Cooling rate | gradient (° C./min) | Tmax Treactor | (° C.) Treactor | Tjacket | (° C.) Treactor | dl10 (µm) | dl50 (µm) | dl90 (µm) |
| 1° C./min | 0.95 | 78 | 63.5 | 60.2 | 77.5 | 156 | 65 | 16 |
| ASAP | 3.2 | 75.7 | 61.2 | 17.5 | 75 | 119 | 36 | 9.2 |
| 0.5° C./min | 0.48 | 75.7 | 63.8 | 62.7 | 75 | 192 | 80 | 20 |

TABLE 1-continued

| | | Crystallization | | | | | |
|---|---|---|---|---|---|---|---|
| | Calculated cooling | | start at ... | start cooling | Particle size distribution | | |
| Cooling rate | gradient (° C./min) | Tmax Treactor | (° C.) Treactor Tjacket | (° C.) Treactor | dl10 (μm) | dl50 (μm) | dl90 (μm) |
| 0.5° C./min | 0.48 | 75.7 | 63.8  62.7 | 75 | 189 | 81 | 23 |
| 0.7° C./min | 0.81 | 75.7 | 61.7  58.9 | 75 | 113 | 41 | 11 |
| 1° C./min | 0.92 | 75.7 | 62.1  54.9 | 75 | 128 | 52 | 13 | b) Formulation of Composition

Table 2 provides the formulation for the F013 formulation. The F011 formulation contained the same ingredients, with the exception of citric acid and NaOH, which were not present in the F011 formulation. Since the F011 formulation does not contain NaOH or citric acid, they are not part of the aqueous phase that is added to the milled concentrate of the F011 formulation. Therefore, the concentration of buffer salts in the aqueous phase of the F011 formulation is slightly different to make the formulation isotonic.

TABLE 2

| | Amount Required | |
|---|---|---|
| Name | Per ml | Quantity for 24 L |
| Paliperidone palmitate (sterile grade) | 156 mg | 3.744 kg |
| Polysorbate 20 parenteral | 12 mg | 288 g |
| Citric acid monohydrate parenteral | 5 mg | 120 g |
| Disodium hydrogen phosphate anhydrous parenteral | 5 mg | 120 g |
| Sodium dihydrogen phosphate monohydrate parenteral | 2.5 mg | 60 g |
| Sodium Hydroxide all use | 2.84 mg | 68 g |
| Polyethylene Glycol 4000 parenteral | 30 mg | 720 g |
| Water for injections q.s. ad | 1000 μl | 24 L |

Equipment
 stainless steel (SS) containers
 Grinding media (Zirconium beads)+stainless steel (SS) grinding chamber
 0.2 μm filters
 40 μm filter
 Filling unit
 Autoclave
 Dry heat oven Manufacturing Zirconium beads were cleaned and rinsed using water for injections and then depyrogenised by dry heat (120 min at 260° C.). Water for injections was transferred into a SS container. Polysorbate 20 was added and dissolved by mixing. The solution was sterilized by filtration through a sterile 0.2 μm filter into a sterilized SS container. Paliperidone palmitate ester (sterile grade) as prepared in the previous examples was dispersed into the solution and mixed until homogeneous. The suspension was milled aseptically in the grinding chamber using Zirconium beads as grinding media until the required particle size was reached. The suspension was filtered aseptically through a 40 μm filter into a sterilized SS container Water for injections was transferred into a SS container, citric acid monohydrate parenteral, disodium hydrogen phosphate anhydrous, sodium dihydrogen phosphate monohydrate, sodium hydroxide all use, polyethylene glycol 4000 were added and mixed until dissolved. This solution was sterilized by filtration through a sterile 0.2 μm filter and transferred aseptically into the suspension. The final suspension was mixed until homogeneous. The suspension was filled aseptically into sterile syringes. The target dose volume was between 0.25 ml and 1.50 ml depending on the dose needed.

TABLE 3

| Dose volume | Target limit | lower limit | upper limit |
|---|---|---|---|
| 0.25 ml-1.00 ml | identical to dose volume | target limit − (target limit × 0.05) | target limit × 1.05 |
| 1.25 ml-1.50 ml | identical to dose volume | target limit − (target limit × 0.025) | target limit × 1.025 |

Sterilization

All aseptic manipulations and sterilization processes were carried out according to FDA and European regulatory guidelines.

Apparatus

Sterilization was done by steam sterilization ($F_0 \geq 15$ of following equipment:
 SS containers
 Zirconium beads+grinding chamber
 0.2 μm filters
 40 μm filter
 filling pump
 Immediate Container
 1 ml long transparent plastic (COC) syringe with luer lock.
 rubber tip cap, FM257/2 dark grey
 rubber plunger stopper, 1 ml long, 4023/50, Fluorotec B2-40
 2.25 ml transparent plastic (COC) syringe with luer lock.
 rubber tip cap, FM257/2 dark grey
 rubber plunger stopper, 1-3 ml, 4023/50, Fluorotec B2-40

The empty syringes with pre-assembled tip-caps were sterilized by gamma-irradiation (dose ≥25 kGy). The rubber plunger stoppers were sterilized by means of steam sterilization ($F_0 \geq 1$).

EXAMPLE 2

Evaluation of the Pharmacokinetic Profile of Gluteal Versus Deltoid Intramuscular Injections of Paliperidone Palmitate 100 mg Equivalent in Patients with Schizophrenia This study was performed to characterize and compare the pharmacokinetic profile of paliperidone palmitate (formulated as described above) following four intramuscular injections in the deltoid or gluteal muscle.

Method

In this multiple-dose, open-label, parallel-group study, patients with schizophrenia were randomized to receive four consecutive intramuscular injections (days 1, 8, 36 and 64) of paliperidone palmitate 100 mg-eq. administered into either the deltoid (n=24) or gluteal muscle (n=25). Plasma samples for pharmacokinetic analyses were collected. The total paliperidone concentration was calculated as the sum of both enantiomers.

Results

The median $C_{max}$ for paliperidone was higher in the deltoid versus the gluteal muscle after the second (31.3 versus 24.1 ng/mL) and fourth (23.7 versus 22.3 ng/mL) injections. After four injections, median $AUC_\infty$ was similar for both injection sites; $C_{max}$ and $AUC_\tau$ for paliperidone were 30% (90% CI=100.56%-168.93%) and 20% (90% CI=93.09%-154.69%) higher in deltoid versus gluteal muscle, respectively. Median $T_{max}$ was similar between injection sites after the second (10 day versus 10 day) and fourth injections (5 versus 6.5 days). After four injections, the median peak-to-trough ratio was higher (2.3 versus 1.9), with a larger intersubject variability for deltoid versus gluteal injection. An increase in median predose plasma concentration between days 8, 36 and 64 for both sites suggested subjects were not completely at steady state after four injections. Relative exposure after the fourth injection was slightly lower than after the second injection in both the deltoid and gluteal muscle. Most commonly reported adverse events (combined injection sites) were orthostatic hypotension (24%), hypotension (14%), diastolic hypotension (12%) and injection site pain (14%). There were four serious adverse events (worsening of psychosis) that led to discontinuations. There were no deaths in the study. Paliperidone palmitate was well tolerated with more favorable local tolerability profile in the gluteal versus deltoid; mean injection site pain VSA score was 3.3 for gluteal versus 10.8 for deltoid muscle (day 1, 8 hours after injection.

Conclusion

Paliperidone palmitate 100 mg-eq. injections resulted in an increased $AUC_\tau$, higher $C_{max}$, greater FI, but similar $T_{max}$ following four consecutive injections into the deltoid versus gluteal muscle. Paliperidone palmitate 100 mg-eq. was systemically and locally well tolerated in this study.

EXAMPLE 3

Assessment of the Dose Proportionality of Paliperidone Palmitate 25, 50, 100, and 150 mg eq. Following Administration in the Deltoid or Gluteal Muscles This study evaluated dose proportionality of paliperidone palmitate injections when administered into either the gluteal or deltoid muscle.

Method

A single-dose, open label, parallel-group study of 201 randomized schizophrenia subjects was performed. The subjects were assigned into eight treatment groups: paliperidone palmitate 25 (n=48), 50 (n=50), 100 (n=51) or 150 (n=52) mg-eq. injected into either the deltoid or gluteal muscle. Serial plasma samples were collected for pharmacokinetic evaluation over 126-day period. The total paliperidone concentration was calculated as the sum of both enantiomers. Dose proportionality was assessed by linear regression model, for each injection site, with log-transformed dose-normalized $AUC_\infty$ and $C_{max}$ as dependent variables and log-transformed dose as predictor, respectively of $C_{max}$ and $AUC_\infty$ ratios of the enantiomers were documented.

Results

Slopes for log-transformed dose-normalized $AUC_\infty$ were not significantly different from zero for deltoid (slope −0.06; p=0.036) and gluteal injections (slope −0.02; p=0.760 indicating a dose-proportional increase in $AUC_\infty$, $T_{max}$, was comparable between doses but slightly earlier for deltoid (13-14 days) versus gluteal injections (13-17 days). Median $C_{max}$ was higher with deltoid (range 5.3-11.0 ng/mL) versus gluteal (range 5.1-8.7 ng/mL) injections except for the 100 mg-eq. deltoid (slope −0.22, p=0.0062) and gluteal (slope −0.31; p<0.0001) injections, indicating a less than dose-proportional increase in $C_{max}$. Results of $C_{max}$ and AUC were confirmed using pairwise comparisons. Plasma concentrations of (+)-enantiomer were consistently higher than (−)-enantiomer; (+)/(−) plasma concentrations ratio was approximately 2.4 shortly after administration and decreased to ~1.7 for both injection sites, independent of dose. After a single dose of paliperidone palmitate, subjects received concomitant oral antipsychotics. Treatment-emergent AEs (TEAs) included tachycardia (10%), headache (7%), schizophrenia (6%), insomnia (5%). Only 2% of subjects discontinued due to TEAs. No deaths were reported.

Conclusion $AUC_\infty$ increased proportionality with increasing paliperidone palmitate doses (5-150 mg-eq.), regardless of gluteal or deltoid injection. Overall, deltoid injection was associated with a higher $C_{max}$ (except for 100 mg-eq.) and slightly earlier $T_{max}$ compared with gluteal injections.

EXAMPLE 4

Comparison of the PK Profile in the Deltoid to that in the Gluteal

The plasma concentration-time profile of paliperidone after single i.m. injection of the paliperidone palmitate formulation at 25-150 mg-eq. has been documented in several studies (Table 4). Details of how the comparison of injection sites study and the dose proportionality studies were performed are provided in Examples 2 and 3.

TABLE 4

Table of Clinical Studies Summarized

| Study | Design/Treatment/PK Objective |
|---|---|
| PHASE 1 STUDIES IN SUBJECTS WITH SCHIZOPHRENIA | |
| R092670-INT-12 (dose-proportionality) | S.D., OL, parallel group/single i.m. injection of F011*, 25, 50, 100 or 150 mg eq./document PK of the F011* formulation at different doses, enantiomer disposition |

TABLE 4-continued

Table of Clinical Studies Summarized

| Study | Design/Treatment/PK Objective |
|---|---|
| PHASE 1 STUDIES IN SUBJECTS WITH SCHIZOPHRENIA | |
| R092670-USA-3 | M.D., OL, randomized, parallel groups/2 i.m. injections of R092670 (F011*) 25 or 150 mg eq., gluteal or deltoid, separated by 1 week/compare the PK after deltoid and gluteal injections, explore the relationship between R092670 PK parameters and CYP P450 genotypes |
| R092670-PSY-1001 (comparison of injection site) | M.D., OL, randomized, parallel groups/4 i.m. injections of R092670 (F013) 100 mg eq. in the gluteal or deltoid muscle (on Day 1, 8, 36 and 64)/compare the PK at steady state between deltoid and gluteal injection sites |
| R092670-PSY-1004 (dose-proportionality) | S.D., OL, randomized, parallel groups/single i.m. injection of R092670 (F013) 25, 50, 100 or 150 mg eq. in the gluteal or deltoid muscle/evaluate dose proportionality of F013 formulation over a dose range of 25-150 mg eq., compare the PK after deltoid and gluteal injections |

S.D.: single dose; M.D.: multiple dose; OL: open-label; DB: double blind; PK: pharmacokinetic; PC: placebo-controlled; AC: active-controlled; pali ER: paliperidone extended release; pali IR: paliperidone immediate release
F011*: Sterilized by gamma-irradiation. Otherwise, sterilized by aseptic crystallization.

The total exposure ($AUC_\infty$) of paliperidone increased proportionally with dose after single-dose injections of 25 to 150 mg eq. paliperidone palmitate in both the deltoid and gluteal muscle. The increase in $C_{max}$ was slightly less than dose proportional for both injections sites at doses greater than 50 mg eq. The apparent half-life (reflecting the absorption rate for this type of formulations) increased with dose from 25 days (median) after the 25 mg eq. dose to 40-49 days (median) after the 100 and 150 mg eq. dose, for both injection sites. The $C_{max}$ of paliperidone was generally higher after single-dose injection of paliperidone palmitate in the deltoid muscle compared to the gluteal muscle (geometric mean ratio ranging from 108.75% to 164.85%) whereas this was much less pronounced for $AUC_\infty$ (geometric mean ratio ranging from 103.00% to 117.83%). The median apparent half-life was comparable between injection sites.

EXAMPLE 5

Description of the PK Profile in the Gluteal After Multiple Administrations

Paliperidone palmitate is a long-acting i.m. injectable, intended to release over a period of 1 month. In order to attain this long injection interval, an ester of paliperidone was prepared that has a limited solubility in a physiological environment. The ester was subsequently formulated as an aqueous suspension for i.m. injection. The rate of dissolution is governed by the particle size distribution whereby it was experimentally determined that an optimal particle size range is contained within xx-yy microm ($d_{50v}$). In fact, the rate of dissolution (and thus the particle size distribution) fully determines the in vivo behaviour, as was nicely demonstrated in study PSY-1002. It was found that the median $C_{max}$ increases and $t_{max}$ shortens with decreasing particle size, which is consistent with the hypothesis that particle size is driving the release rate. The point estimates suggest that paliperidone exposure (AUC, $C_{max}$) after injection of paliperidone palmitate is similar between the to-be-marketed formulation F013 and formulation F011.

TABLE 5

Table of Clinical Studies Summarized in Module 2.7.2

| Study | Design/Treatment/PK Objective |
|---|---|
| PHASE 1 STUDIES IN SUBJECTS WITH SCHIZOPHRENIA | |
| R092670-BEL-4 (pilot, dose-proportionality) | M.D., OL, sequential, parallel groups/4-6 monthly i.m. injections of F004, 50 mg eq. or 100 mg eq. or 150 mg eq./explore M.D. PK and dose-proportionality |
| R092670-BEL-7 (dosing regimen) | M.D., OL, parallel groups/F004 formulation: Panel I: 100 mg eq. i.m. followed by 3 monthly i.m. injections of 50 mg eq.; Panel II: 200 mg eq. i.m. followed by 3 monthly i.m. injections of 100 mg eq.; Panel III: 300 mg eq. i.m. followed by 3 monthly i.m. injections of 150 mg eq.; Panel IV: 50 mg eq. i.m. followed by 1 week later by 4 monthly i.m. injections of 50 mg eq.; Panel V: 150 mg eq. i.m. followed by 1 week later by 4 monthly i.m. injections of 150 mg eq./explore the M.D. PK with various dosing regimens |
| R092670-INT-11 (compare F004 and F011) | M.D., DB, randomized, 4-group 2-way cross-over/4 monthly i.m. injections of F004 or F011*, 2 × 50 and 2 × 150 mg eq./compare PK of F004 and F011* formulations; compare S.D. and M.D. PK of both formulations |
| R092670-PSY-1002 (IVIVC) | S.D., OL, randomized, parallel groups/single i.m. injections of 1 mg paliperidone IR, followed by single i.m. injection of 50 mg eq. R092670: 1 of 4 F013 formulations with different particle sizes, or |

TABLE 5-continued

Table of Clinical Studies Summarized in Module 2.7.2

| Study | Design/Treatment/PK Objective |
|---|---|
| | PHASE 1 STUDIES IN SUBJECTS WITH SCHIZOPHRENIA |
| R092670-PSY-1001 (comparison of injection site) | F011 formulation with medium particle size/explore IVIVC of 4 F013 formulations, compare the PK of F011 and F013 formulations M.D., OL, randomized, parallel groups/4 i.m. injections of R092670 (F013) 100 mg eq. in the gluteal or deltoid muscle (on Day 1, 8, 36 and 64)/compare the PK at steady state between deltoid and gluteal injection sites |

S.D.: single dose; M.D.: multiple dose; OL: open-label; DB: double blind; PK: pharmacokinetic; PC: placebo-controlled; AC: active-controlled; pali ER: paliperidone extended release; pali IR: paliperidone immediate release
F011*: Sterilized by gamma-irradiation. Otherwise, sterilized by aseptic crystallization.

Pharmacokinetic theory also implies that for a formulation with such a long apparent half-life it takes 4-5 times this half-life for steady-state to be achieved. For individual patients, this means that following the first few injections, only subtherapeutic plasma concentrations are achieved. In order to overcome this problem, a loading dose regimen was developed (BEL-7), that was subsequently used in phase 2 and 3 of drug development. The dosing regimen consisting of two initial i.m. injections separated by one week followed by subsequent doses at monthly intervals resulted in a faster attainment of apparent steady state compared with a dosing regimen of one initial injection of twice the monthly dose followed by subsequent doses at monthly intervals. Somewhat higher peak-to-through fluctuations were observed with the first dosing regimen as compared with the latter one. The dosing regimen consisting of two initial i.m. injections separated by one week followed by subsequent doses at monthly intervals was selected for further studies and is also the recommended regimen for treatment.

EXAMPLE 6

Description of the Exposure Range Needed for Efficacy Using Invega Data

All antipsychotic drugs currently on the market have one feature in common: they antagonize the $D_2$ receptor at the level of the brain. It has been empirically derived and is currently widely excepted that 65-70% occupancy is needed for antipsychotics to show clinical efficacy (Farde et al.), i.e. improvement on the PANSS scale. A too high occupancy (80-85%) will typically increase the risk to develop EPS. In order to determine the central $D_2$ occupancy, PET trials in human healthy volunteers are typically performed. Two such studies have been done for paliperidone: SWE-1 and SIV-101, showing that the $K_D^{app}$ for $D_2$ occupancy was ranging from 4.4 to 6.4 ng/mL. Using the 65-85% occupancy window, it can be calculated that the exposure range for efficacy without an increased risk to develop EPS as compared to placebo (<5% difference in probability) is contained in the window of 7.5-40 ng/mL.

In addition, based on the results of the phase 3 program of 6 mg paliperidone ER, in which plasma samples were collected at several time points, a plasma concentration of 7.5 ng/mL was identified as the cut-off value above which 90% of the plasma concentrations were observed. The risk to develop EPS was clearly higher for dose above 9 mg Invega. Calculating back, this roughly corresponds to an exposure level of 35-40 ng/mL at steady-state. This implies that there is ample evidence to support a target exposure efficacy range of 7.5-40 ng/mL. This should be the target exposure range for paliperidone after injection of the paliperidone palmitate formulation.

EXAMPLE 7

Optimal Way of Dosing

During the development of paliperidone palmitate, as the result of an extensive population PK analysis (refer to popPK report for paliperidone palmitate), several factors were found to slow down the release of paliperidone from the formulation, resulting in a slower build-up of plasma concentrations at the start of therapy and in more time required to reach steady-state. One factor was body mass index: the higher the BMI, the slower the dissolution (probably related to local physiological factors such as diminished blood flow at the site of injection); the other one being volume administered: the higher the volume injected, the slower the dissolution (probably related to the nonlinear relationship between surface area and volume). This has resulted in a lower than expected exposure using the originally proposed loading dose regimen, and the need to come up with an improved loading dose scheme for all patients irrespective of BMI in order to avoid drop-out due to lack of efficacy at the start of therapy. The aim was to get patients as quickly as possible above the 7.5 ng/mL, certainly after 1 week for all doses considered (25 mg-eq. and above).

Simulation scenarios with the statistically significant covariates from the population PK analysis revealed the following features about the paliperidone PK after injection of paliperidone palmitate:
  Compared to deltoid injections, repeated administration in the gluteal muscle resulted in a delayed time to achieve steady-state (~4 wk longer), but did not influence the overall exposure (in terms of steady-state concentrations) to paliperidone.
  Deltoid injections resulted in a faster rise in initial plasma concentrations, facilitating a rapid attainment of potential therapeutic plasma concentrations. The deltoid injection site is therefore recommended as the initiation site for dosing paliperidone palmitate.
  Higher doses, associated with larger injection volumes, increased the apparent half-life of paliperidone, which in turn increased the time to achieve steady-state.
  Needle length was an important variable for the absorption kinetics from the deltoid injection-site and it is recommended to use a longer 1.5-inch needle for deltoid administration in heavy subjects (≥90 kg). Simulations indicated that the use of a longer needle in the deltoid muscle for the heavy individuals might be associated with an initial faster release of paliperidone into the systemic circulation, which could help overcome the slower absorption observed in heavier individuals described below.

The body size variable BMI was another important covariate for paliperidone palmitate. A slower rise in initial concentrations was observed in the obese population, which possibly occurred due to the reduced speed of initial influx from the injection site. Initiating the first two injections in the deltoid muscle and using a longer 1.5-inch needle for deltoid injection in heavy subjects can mitigate this effect. These observations are consistent with the expectation that in heavy subjects, administration into the adipose layer of the deltoid muscle can be avoided with the use of a longer injection needle.

Summarize what the optimized loading dose regimens would be here:
  150 deltoid (day 1), 100 mg deltoid (day 8), then every 4 weeks maintenance (gluteal or deltoid) (PSY-3006, simulations—popPK report palmitate)
  100 deltoid (day 1), 100 mg deltoid (day 8), then every 4 weeks maintenance (gluteal or deltoid) (simulations—popPK report palmitate, proposed for the label)
  150 mg deltoid day 1, maintenance dose day 8 and then every 4 weeks (gluteal or deltoid) (PSY-3007)

EXAMPLE 8

Title of Study:
  A Randomized, Double-Blind, Placebo-Controlled, Parallel-Group, Dose-Response Study to Evaluate the Efficacy and Safety of 3 Fixed Doses (25 mg eq., 100 mg eq., and 150 mg eq.) of Paliperidone Palmitate in Subjects With Schizophrenia Phase of Development:
  Phase 3

Objectives:
  The primary objectives of this study were to evaluate the efficacy and safety of 3 fixed doses of paliperidone palmitate administered intramuscularly (i.m.) after an initial dose of 150 mg equivalent (eq.) in the deltoid muscle followed by either deltoid or gluteal injections for a total of 13 weeks of treatment as compared with placebo in subjects with schizophrenia.
  The secondary objectives were to:
    Assess the benefits in personal and social functioning (key secondary endpoint) associated with the use of paliperidone palmitate compared with placebo;
    Assess the global improvement in severity of illness associated with the use of paliperidone palmitate compared with placebo;
    Assess the dose-response and exposure-response relationships of paliperidone palmitate.

Methods:
  This was a randomized, double-blind, placebo-controlled, parallel-group, multicenter, dose-response study of men and women, 18 years of age and older, who had a Diagnostic and Statistical Manual of Mental Disorders, Fourth Edition (DSM-IV) diagnosis of schizophrenia. The study included a screening period of up to 7 days and a 13-week double-blind treatment period. The screening period included a washout of disallowed psychotropic medications.
  Subjects without source documentation of previous exposure to at least 2 doses of oral risperidone or paliperidone extended-release (ER), at least 1 dose of i.m. RISPERDAL® CONSTA® or paliperidone palmitate, or who were not currently receiving an antipsychotic medication were given 4 to 6 days of paliperidone ER 6 mg/day (or the option of oral risperidone 3 mg/day for subjects in Malaysia) for tolerability testing. Subjects who had source documentation of previous exposure to the above medications and were currently taking another antipsychotic regimen continued their current treatment through Day-1. At the beginning of the double-blind treatment period, subjects were randomly assigned in a 1:1:1:1 ratio to 1 of 4 treatment groups: placebo or paliperidone palmitate 25 mg eq., 100 mg eq., or 150 mg eq. Study medication was administered as 4 doses: an initial i.m. injection of 150 mg eq. of paliperidone palmitate or placebo followed by 3 fixed i.m. doses of placebo or paliperidone palmitate [25, 100, or 150 mg eq.] on Days 8, 36, and 64. The initial injection of study medication was given in the deltoid muscle. Subsequent injections were given either in the deltoid or gluteal muscle at the discretion of the investigator. Randomized subjects were to remain in the study for 28 days after the last injection on Day 64 with the end of study visit scheduled for Day 92 during the double-blind period. The entire study, including the screening period, lasted approximately 14 weeks. Samples for pharmacokinetic (PK) evaluation were collected on Day 1, prior to the first injection and on Days 2, 4, 6, 8, 15, 22, 36, 64 and 92. Efficacy and safety were evaluated regularly throughout the study. A pharmacogenomic blood sample (10 mL) was collected from subjects who gave separate written informed consent for this part of the study. Participation in the pharmacogenomic research was optional. Approximately 105 to 115 mL of whole blood was collected during the study.

Number of Subjects (Planned and Analyzed):
  It was planned to include approximately 644 men and women in this study. A total of 652 eligible subjects from 72 centers in 8 countries were randomized and received at least 1 dose of double-blind study medication (safety analysis set); 636 subjects had both baseline and post baseline efficacy data (intent-to-treat analysis set).

Diagnosis and Main Criteria for Inclusion:
  Male or female subjects ≥18 years of age who met the DSM-IV diagnostic criteria for schizophrenia for at least 1 year before screening, had a Positive and Negative Syndrome Scale (PANSS) total score at screening of between 70 and 120, inclusive, and at baseline of between 60 and 120, inclusive, and had a body mass index (BMI) of >17.0 kg/m$^2$ to <40 kg/m$^2$ were eligible.

Test Product, Dose and Mode of Administration, Batch No.:
  Paliperidone ER was supplied as a 6-mg capsule-shaped tablet for the oral tolerability test (batch number 0617714/F40). Paliperidone palmitate was supplied as 25, 100, or 150 mg eq. injectable suspension (batch numbers 06K22/F13 and 07D23/F13). For the oral tolerability test, a 6-mg tablet of paliperidone ER (or the option of oral risperidone 3 mg/day for subjects in Malaysia) was administered daily for 4 to 6 days. On Day 1 of the double-blind treatment period, 150 mg eq. of paliperidone palmitate was injected in the deltoid muscle followed by 25, 100, or 150 mg eq. i.m. injections of paliperidone palmitate on Days 8, 36, and 64, injected into the deltoid or gluteal muscle at the investigator's discretion.

Reference Therapy, Dose and Mode of Administration, Batch No.:
  Placebo was supplied as 20% Intralipid (200 mg/mL) injectable emulsion (batch numbers 06K14/F00 and 07F12/F00). An injection was given on Days 1, 8, 36 and 64.

Duration of Treatment:
  The study consisted of a screening and washout phase of 7 days and a double-blind treatment period of 13 weeks, starting with the first injection in the deltoid muscle followed by a second injection 1 week later. All injections after Day 1 were given in either the deltoid or the gluteal muscle at the discretion of the investigator. Two subsequent injections were given at 4-week intervals.

Criteria for Evaluation:
Pharmacokinetic Evaluations:

A sparse blood sampling procedure was followed to study the paliperidone concentration-time profiles. Paliperidone plasma concentration-time data were subject to population PK analysis using nonlinear mixed-effects modeling, and details are described in a separate report.

Efficacy Evaluations/Criteria:

The primary endpoint was the change in the PANSS total score from baseline (i.e., the start of double-blind treatment, Day 1) to the end of the double-blind treatment period (i.e., Day 92 or the last post baseline assessment). The key secondary efficacy endpoint was the change in the Personal and Social Performance Scale (PSP) from baseline to the end of the double-blind treatment period. The other secondary efficacy endpoint was the change in the Clinical Global Impression-Severity (CGI-S) scores from baseline to the end of the double-blind treatment period. Other endpoints included the change from baseline in subject ratings of sleep quality and daytime drowsiness using a visual analogue scale (VAS), the onset of therapeutic effect, responder rate, and the change from baseline to end point in PANSS subscales and Marder factors.

Safety Evaluations:

Safety was monitored by the evaluation of adverse events, extrapyramidal symptom (EPS) rating scales (Abnormal Involuntary Movement Scale [AIMS], Barnes Akathisia Rating Scale [BARS], Simpson and Angus Rating Scale [SAS]) scores, clinical laboratory test results, vital signs measurements, electrocardiograms (ECGs), and physical examination findings. In addition, the tolerability of injections was assessed; the investigators evaluated injection sites and the subjects assessed injection pain.

Statistical Methods:

All randomized subjects who received at least 1 dose of double-blind study drug and had both baseline and at least one post baseline efficacy measurement (PANSS, PSP, or CGI-S) during the double-blind treatment period were included in the intent-to-treat efficacy analyses. The overall type I error rate for testing all paliperidone palmitate doses versus placebo for both the primary endpoint (change in PANSS total score at end point) and the key secondary efficacy endpoint (change in PSP total score at end point) was controlled at the 2-sided 0.05 significance level. The 2 families of hypotheses (in each family, 3 comparisons for each of the paliperidone palmitate doses versus placebo) were tested using a parallel gatekeeping procedure that adjusts for multiplicity using Dunnett's method in each family of hypotheses and using Bonferroni's inequality between different families of hypotheses. This procedure is referred to as the Dunnett-Bonferroni-based parallel gatekeeping procedure.

The change from baseline in PANSS total score at each visit and at end point was analyzed using an analysis of covariance (ANCOVA) model. The last observation carried forward (LOCF) method was used. The model included treatment and country as factors and baseline PANSS total score as a covariate. Treatment effect was based on the difference in least-squares mean change. Dunnett's test was used to adjust for multiple comparisons of the 3 paliperidone palmitate dosages versus placebo. Unadjusted 2-sided 95% confidence intervals were presented for the difference in least-squares mean change of each paliperidone palmitate dosage group compared with placebo. Treatment-by-country and treatment-by-baseline PANSS total score interactions were explored using the same ANCOVA model as the one for the analysis of the primary endpoint. If either term was statistically significant at the predefined 2-sided significance level of 0.10, further evaluations of the effect of other covariates were to be performed to assess the nature of the interaction and identify possible causes. In addition, to address the dose-response relationship and to facilitate the discussion of dosage selection, an analysis to compare the 3 active paliperidone palmitate dosages with each other was performed without adjustment for multiple comparisons.

The analysis of the key secondary endpoint, change in PSP score at end point, was conducted by means of an ANCOVA model with treatment and country as factors and the baseline score as the covariate. The Dunnett-Bonferroni-based parallel gatekeeping approach was used to adjust for multiple testing.

Between-group comparisons of CGI-S were performed by using an ANCOVA model on the ranks of change from baseline, with treatment and country as factors and the baseline score as the covariate.

Change from baseline over time (observed case) in the PANSS total score was explored using mixed effects linear models for repeated measures with time, treatment, country, and treatment-by-time as factors and baseline score as a covariate.

The number and percentage of subjects with treatment-emergent adverse events were summarized. Adverse events of potential clinical interest were summarized separately, including events related to EPS or changes in serum glucose or prolactin levels.

Changes from baseline in clinical laboratory tests, vital sign measurements, ECGs, body weight, BMI, and EPS scale scores were summarized by treatment group. Prolactin levels were summarized by sex. Subjects with potentially abnormal values or changes in clinical laboratory tests, vital signs, orthostatic parameters, and ECG parameters were summarized based on predefined criteria. Frequency distributions were presented for the investigator's evaluation of the injection site, and descriptive statistics were presented for VAS scores corresponding to the subject's evaluation of injection pain.

Results:

The majority of subjects in the paliperidone palmitate treatment groups (56%-61%) received all 4 injections compared with 48% of the placebo-treated subjects. Completion rates were also higher for the paliperidone palmitate groups (52%-55%) than for the placebo group (43%). More subjects were discontinued for lack of efficacy in the placebo group (27%) compared with the paliperidone palmitate groups (14%-19%).

Demographic and Baseline Characteristics:

The double-blind treatment groups were well matched with respect to demographic and baseline disease characteristics and psychiatric history. The 636 subjects who comprised the intent-to-treat analysis set were mainly male (67%), racially diverse (54% White, 30% Black, 14% Asian, 1% other races), and predominately between the ages of 26 and 50 years (75%). Most subjects had a primary diagnosis of paranoid schizophrenia (88%), and were highly symptomatic as indicated by a mean PANSS total score of 87.1 at baseline. There were notable differences between countries with respect to BMI and gender, with subjects enrolled at centers in the U.S. being more likely to be male and obese (i.e., BMI≥30 kg/m$^2$) than those from centers in other countries.

Pharmacokinetics:

A total of 488 subjects who were randomly assigned to receive paliperidone palmitate treatment had scheduled pharmacokinetic blood samples taken over the course of the study. The median paliperidone predose concentration for the 25 mg eq. treatment group was highest on Day 8, which is the result of the initial 150 mg eq. dose on Day 1. After Day 8, paliperidone concentrations decreased and seemed to reach steady state levels on Day 92 based on visual inspection. The median paliperidone predose concentration for the 100 mg eq. treatment group remained in the same range from Day 8 onwards. The median predose concentration for the 150 mg eq. treatment group seemed to increase up to the last study day, Day 92. The median paliperidone plasma concentrations on Day 8 were lower in subjects with high BMI ($\geq 25$ to $<30$ kg/m$^2$ and $\geq 30$ kg/m$^2$; overweight/obese) compared to subjects with low BMI ($<25$ kg/m$^2$) for the 3 dose groups. After Day 8, no consistent trends were observed for the 3 paliperidone palmitate dose groups with respect to paliperidone plasma concentrations as a function of baseline BMI classification.

The mean and median paliperidone plasma concentrations on Day 64 for the 100 mg eq. treatment group were approximately 2-fold higher than those for the 25 mg eq. treatment group. Thus, the PK profile for the 25 mg eq. and 100 mg eq. dose groups appeared to be less than dose proportional, which is the result of the initial paliperidone palmitate 150 mg eq. injection on Day 1 in all active treatment groups. The mean and median paliperidone plasma concentrations on Day 64 for the 100 mg eq. dose were apparently dose proportional compared to the 150 mg eq. dose. A high inter-subject variability was observed in the paliperidone plasma concentrations on Days 1 and 2 with a % CV of 118.9% (Day 1) and 153.1% (Day 2). After Day 2, the inter-subject variability decreased and the % CV ranged from 50.4 to 83.4%.

Primary Efficacy Analysis:

Adult subjects with schizophrenia achieved statistically significant improvements in the PANSS total score (primary efficacy endpoint) with all 3 doses of paliperidone palmitate compared to placebo (25 mg eq.: p=0.034; 100 mg eq.: p<0.001; 150 mg eq.: p<0.001) based on the intent-to-treat LOCF analysis and the Dunnett's test to control for multiplicity.

exploratory analysis additionally provided no statistical evidence for a BMI effect on treatment.

All 3 paliperidone palmitate dose groups showed a statistically significant improvement over placebo in the change in PANSS total score as of Day 22 and at every subsequent time point, and as early as Day 8 in the paliperidone palmitate 25 mg eq. and 150 mg eq. groups.

The mean improvements in the PSP score from baseline to end point, the key secondary efficacy outcome measure, showed a dose response among the 3 paliperidone palmitate groups (25 mg eq.: 2.9; 100 mg eq.: 6.1; 150 mg eq.: 8.3); all were numerically higher than the mean improvement in the PSP score seen in the placebo group (1.7). Based on the intent-to-treat LOCF analysis of this key secondary efficacy variable, using the Dunnett-Bonferroni-based parallel gatekeeping procedure to adjust for multiplicity, the improvement in the paliperidone palmitate 100 and 150 mg eq. treatment groups reached statistical significance (100 mg eq.: p=0.007; 150 mg eq.: p<0.001) when compared with the placebo group.

The paliperidone palmitate 100 mg eq. and 150 mg eq. groups were statistically significantly superior to placebo in improving the CGI-S scores from baseline to end point (LOCF) (without multiplicity adjustment, 100 mg eq.: p=0.005; 150 mg eq.: p<0.001). Significantly more subjects treated with paliperidone palmitate 25 mg eq. (33.5%; p=0.007), 100 mg eq. (41.0%; p<0.001), and 150 mg eq. (40.0%, p<0.001) achieved responder status (30% or larger decrease on PANSS total scores) than with placebo (20.0%).

Based on the intent-to-treat LOCF analysis of the change from baseline to end point without statistical adjustment for multiplicity, the paliperidone palmitate 100 and 150 mg eq. groups were statistically significantly superior to the placebo group for all 5 PANSS Marder factors (p<0.010). The improvements in both negative symptoms and disorganized thoughts factor scores were statistically significantly greater in the paliperidone palmitate 25 mg eq. group compared with placebo (p=0.032).

Positive and Negative Syndrome Scale for Schizophrenia (PANSS) Total Score - Change from Baseline to End Point-LOCF with the Dunnett-Bonferroni-Based Parallel Gatekeeping Procedure (Study R092670-PSY-3007: Intent-to-Treat Analysis Set)

|  | Placebo (N = 160) | R092670 25 mg eq. (N = 155) | R092670 100 mg eq. (N = 161) | R092670 150 mg eq. (N = 160) |
|---|---|---|---|---|
| Baseline Mean (SD) | 86.8 (10.31) | 86.9 (11.99) | 86.2 (10.77) | 88.4 (11.70) |
| End point Mean (SD) | 83.9 (21.44) | 78.8 (19.88) | 74.6 (18.06) | 75.2 (18.59) |
| Change from Baseline |  |  |  |  |
| Mean (SD) | −2.9 (19.26) | −8.0 (19.90) | −11.6 (17.63) | −13.2 (18.48) |
| P-value (minus Placebo)[a] |  | 0.034 | <0.001 | <0.001 |
| Diff of LS Means (SE) |  | −5.1 (2.01) | −8.7 (2.00) | −9.8 (2.00) |

[a]Based on analysis of covariance (ANCOVA) model with treatment (Placebo, R092670 25 mg eq., R092670 100 mg eq., R092670 150 mg eq.) and country as factors, and baseline value as a covariate. P-values were adjusted for multiplicity for comparison with placebo using Dunnett's test.
Note:
Negative change in score indicates improvement.

Other Efficacy Results:

There was a dose-response pattern with respect to the primary efficacy variable, with the mean decreases (improvement) in the PANSS total score at end point (LOCF).

Prespecified treatment-by-country and treatment-by-baseline PANSS total score interactions in the primary efficacy model were not statistically significant at the 0.10 level. An Based on the intent-to-treat LOCF analysis using an ANCOVA model with no adjustment for multiplicity, the mean improvement in sleep quality in the paliperidone palmitate 100 mg eq. and 150 mg eq. groups were statistically significant (p<0.001 and p=0.026, respectively) when compared with placebo. The mean changes in daytime drowsiness in the paliperidone palmitate treatment groups were not statistically significantly different from that in the placebo group (25 mg eq.: p=0.541; 100 mg eq.: p=0.340; 150 mg eq.: p=0.261).

Safety Results:

Paliperidone palmitate, injected at a dose of 150 mg eq. into the deltoid muscle followed by 3 i.m. injections at fixed doses of 25 mg eq., 100 mg eq., or 150 mg eq. on Days 8, 36, and 64, was generally well tolerated by adult subjects with schizophrenia during this 13-week study. Overall, the safety and tolerability results were consistent with previous clinical studies involving paliperidone palmitate, and no new safety signals were detected.

The overall summary of treatment-emergent adverse events is given below.

The incidence of treatment-emergent EPS-related adverse events was low and comparable to placebo. Akathisia was the most frequently reported EPS-related adverse event (4.9% for the placebo group and 1.3%, 4.8%, 5.5% for the paliperidone palmitate 25, 100, and 150 mg eq. groups, respectively). None of the EPS-related adverse events reported in subjects receiving paliperidone palmitate were serious or treatment limiting, and only 1 was severe (musculoskeletal stiffness). Results of EPS rating scales and use of anti-EPS medication were consistent in indicating that paliperidone palmitate was associated with a low incidence of EPS.

Overall Summary of Treatment-Emergent Adverse Events
(Study R092670-PSY-3007: Safety Analysis Set)

|  | Placebo (N = 164) n (%) | R092670 25 mg eq. (N = 160) n (%) | R092670 100 mg eq. (N = 165) n (%) | R092670 150 mg eq. (N = 163) n (%) | Total (N = 652) n (%) |
|---|---|---|---|---|---|
| TEAE | 107 (65.2) | 101 (63.1) | 99 (60.0) | 103 (63.2) | 410 (62.9) |
| Possibly related TEAE[a] | 47 (28.7) | 45 (28.1) | 49 (29.7) | 51 (31.3) | 192 (29.4) |
| TEAE leading to death | 0 | 0 | 0 | 1 (0.6) | 1 (0.2) |
| 1 or more serious TEAE | 23 (14.0) | 15 (9.4) | 22 (13.3) | 13 (8.0) | 73 (11.2) |
| TEAE leading to permanent stop | 11 (6.7) | 10 (6.3) | 10 (6.1) | 13 (8.0) | 44 (6.7) |

[a]Study drug relationships of possible, probable, and very likely are included in this category.
Adverse events are coded using MedDRA version 10.1

There was 1 death in a subject in the paliperidone palmitate 150 mg eq. group after withdrawal from the study due to an adverse event (cerebrovascular accident) that began during the study. This subject received 2 injections of study medication, with the last injection administered approximately 2 weeks before the subject died. While this event was assessed as doubtfully related to study treatment by the investigator, an unblinded review by the sponsor assessed this event to be possibly related to study treatment.

The number of subjects who experienced treatment-emergent serious adverse events was higher in the placebo group than in any of the paliperidone palmitate groups (see table above). Most serious adverse events in all treatment groups were psychiatric disorders (e.g., schizophrenia, psychotic disorder) that were likely the result of the natural course of the underlying schizophrenia. Adverse events leading to study discontinuation occurred at a similar low incidence across treatment groups.

Common treatment-emergent adverse events (≥2% of subjects in any treatment group) that occurred more frequently in the total paliperidone palmitate group (all 3 active dose groups combined) than in the placebo-treated subjects (i.e., ≥1% difference between the combined paliperidone palmitate group and the placebo group) were: injection site pain, dizziness, sedation, pain in extremity, and myalgia. An examination of treatment-emergent adverse events of potential clinical importance revealed no reports of seizure or convulsion, tardive dyskinesia, dermatologic events, neuroleptic malignant syndrome, hyperthermia, anaphylactic reaction, rhabdomyolysis, syndrome of inappropriate secretion of antidiuretic hormone, ventricular tachycardia, ventricular fibrillation, or torsades de pointes.

In general, the type and incidence of treatment-emergent adverse events did not differ as a function of baseline BMI categories (normal: <25 kg/m$^2$; overweight: ≥25 to <30 kg/m$^2$; obese: ≥30 kg/m$^2$).

No clinically relevant mean changes from baseline to end point in supine or standing pulse rates were apparent for any of the paliperidone palmitate doses. A similar, low percentage of subjects had pulse rate of ≥100 bpm with an increase of ≥15 bpm in the placebo and paliperidone palmitate groups (6% to 11% for standing measurements; 2% to 5% for supine measurements).

Assessment of ECG data did not demonstrate evidence of clinically significant QTc prolongation with paliperidone palmitate at doses up to 150 mg eq. No subject had a maximum QTcLD value >480 ms or a maximal change in QTcLD >60 ms during the study.

The increases in body weight with paliperidone palmitate over the 13-week double-blind treatment period were modest in a dose-related manner, averaging 0.4, 0.7, and 1.4 kg for the 25 mg eq., 100 mg eq., and 150 mg eq. groups, respectively (−0.2 kg for placebo); corresponding mean changes in BMI from baseline to end point were 0.1, 0.3, and 0.5 kg/m$^2$, respectively (−0.1 kg/m$^2$ for placebo). A clinically relevant weight increase of at least 7% relative to baseline was seen in 13% of subjects receiving the highest dose of paliperidone palmitate (compared with 5% for placebo).

Consistent with the known pharmacology of paliperidone, increases in prolactin levels were observed with greater frequency in subjects who received paliperidone palmitate, with the largest increase seen in the 150 mg eq. group. Overall, there was a low incidence of potentially prolactin-related adverse events, despite the known propensity of paliperidone palmitate to increase serum prolactin levels. This suggests that the clinical importance of this increase in serum prolactin levels is of questionable clinical significance.

Based on mean changes from baseline to end point and the occurrence of treatment-emergent markedly abnormal laboratory test values and adverse events related to abnormal laboratory analyte findings, except for prolactin, the effects of paliperidone palmitate on the results of chemistry and hematology laboratory tests (including liver and renal function tests, serum lipid levels, and glucose levels) did not show clinically relevant differences from those of placebo.

Local injection site tolerability was good. Occurrences of induration, redness, or swelling as assessed by blinded study personnel were infrequent, generally mild, decreasing over time, and similar in incidence for the paliperidone palmitate and placebo groups. Investigator ratings of injection pain were similar for the placebo and paliperidone palmitate groups.

Study Limitations:

This study investigated the efficacy and safety of paliperidone palmitate for acute treatment of schizophrenia over 13 weeks and does not provide information on longer term treatment. The study was not designed to detect differences between doses of paliperidone palmitate; thus, dose-related trends in efficacy and safety can only be described descriptively. The study was also not designed to demonstrate efficacy for specific subgroups of subjects, such as those from a particular country. An independent, centralized blinded rating service was used for performing all ratings of PANSS, PSP and CGI-S for all subjects enrolled at U.S. sites. The investigators at these sites did not complete any of the ratings, which would have provided a reference for ratings provided by the rating service. Thus, data from this study cannot be used to fully evaluate the utility of using blinded independent raters for detecting treatment differences.

Conclusion:

All 3 doses of paliperidone palmitate tested in this study—25, 100, and 150 mg eq.—were efficacious in adult subjects with schizophrenia who were experiencing acutely exacerbated schizophrenia. Specifically, the results of the primary efficacy endpoint (change from baseline to end point in PANSS total score) demonstrated statistical superiority of paliperidone palmitate 25 mg eq., 100 mg eq., and 150 mg eq. over placebo. Significantly greater improvement in subjects' personal and social functioning (as measured by the PSP score) was also seen for the paliperidone palmitate 100 mg eq. and 150 mg eq. doses compared with placebo, and global improvement was validated by a favorable and statistically significant CGI-S change for these 2 dose groups. There was a dose response in the primary and secondary efficacy endpoints (PANSS, PSP, and CGI-S). All 3 doses of paliperidone palmitate, including the highest dose of 150 mg eq., were well tolerated, suggesting a positive benefit-risk ratio across the dose range currently studied. No new safety signal was detected.

FIGURES

Figure 2:
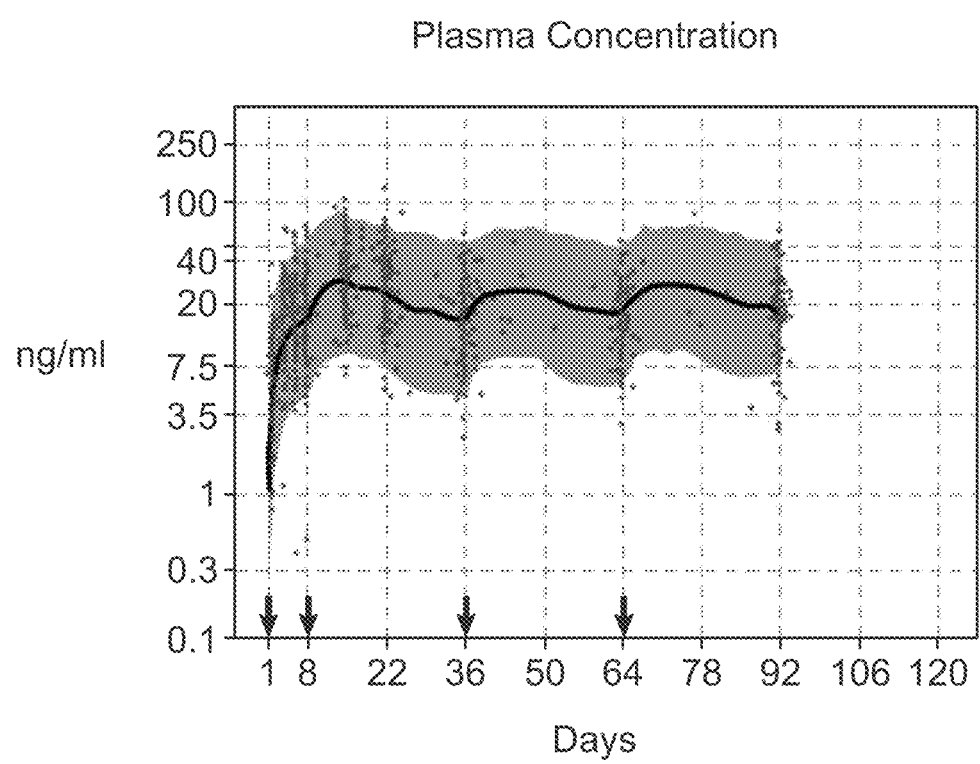
FIG. 2 shows the observed versus the population pharmacokinetics model simulation for plasma paliperidone concentrations for paliperidone palmitate 150 mg eq. in the deltoid on day 1, followed by 100 mg eq. in either the deltoid or gluteus on days 8, 36, and 64.
Figure 3:
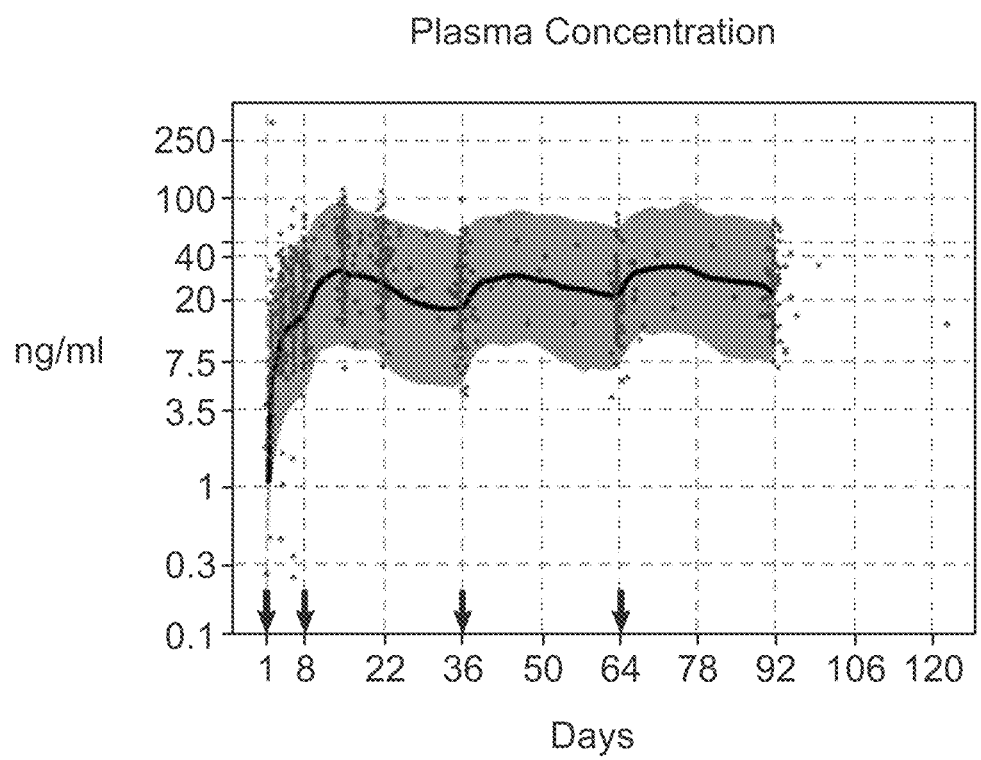
FIG. 3 shows the observed versus the population pharmacokinetics model simulation for plasma paliperidone concentrations for paliperidone palmitate 150 mg eq. in the deltoid on day 1, followed by 150 mg eq. in either the deltoid or gluteus on days 8, 36, and 64.

FIGS. 1-3 graphically presents the observed versus population pharmacokinetics model simulation for plasma paliperidone concentrations. The line indicates the median values calculated from population pharmacokinetic simulation. The shading indicates 90% prediction interval representing the between and within subject, variability obtained using the population pharmacokinetic simulation. The circles indicate observed plasma paliperidone concentrations. The arrows indicate the days when paliperidone palmitate injection was given. As is apparent from the Figures the plasma profiles provided by initiating paliperidone with 150 mg eq. followed by a subsequent dose of 100 or 150 for days 1-36 provide a rapid rise to a therapeutic dose levels. Most preferably the dosing of paliperidone to patients should be maintained within ±25%, preferably 20% of the median plasma concentrations provided in these figures for days 1-36. For patients whose dosing continues at 100 mg eq. the preferably the dosing of paliperidone to patients should be maintained within ±25%, preferably 20% of the median plasma concentrations provided in FIG. 2 for days 1-64. For patients whose dosing continues at 150 mg eq. the preferably the dosing of paliperidone to patients should be maintained within ±25%, preferably 20% of the median plasma concentrations provided in FIG. 3 for days 1-64.

We claim:

1. A dosing regimen for administering paliperidone palmitate to a psychiatric patient in need of treatment for schizophrenia, schizoaffective disorder, or schizophreniform disorder comprising
    (1) administering intramuscularly in the deltoid of a patient in need of treatment a first loading dose of about 150 mg-eq. of paliperidone as paliperidone palmitate formulated in a sustained release formulation on the first day of treatment;
    (2) administering intramuscularly in the deltoid muscle of the patient in need of treatment a second loading dose of about 100 mg-eq. of paliperidone as paliperidone palmitate formulated in a sustained release formulation on the $6^{th}$ to about 10th day of treatment; and
    (3) administering intramuscularly in the deltoid or gluteal muscle of the patient in need of treatment a first maintenance dose of about 25 mg-eq. to about 150 mg-eq. of paliperidone as paliperidone palmitate in a sustained release formulation a month (±7 days) after the second loading dose.

2. The dosing regimen of claim 1 wherein after administration of the first maintenance dose, subsequent maintenance doses of from about 25 mg-eq. to 150 mg-eq. are administered in the deltoid or gluteal muscle of the psychiatric patient in need of treatment at monthly (±7 days) intervals.

3. The dosing regimen of claim 1 wherein the sustained release formulation is an aqueous nanoparticle suspension.

4. A dosing regimen for administering paliperidone palmitate to a psychiatric patient in need of treatment for psychotic disorder comprising
    (a) administering intramuscularly in the deltoid of a patient in need of treatment a first loading dose of about 150 mg-eq. of paliperidone as paliperidone palmitate formulated in a sustained release formulation on the first day of treatment;
    (b) administering intramuscularly in the deltoid muscle of the patient in need of treatment a second loading dose of about 100 mg-eq. of paliperidone as paliperidone palmitate formulated in a sustained release formulation on the eighth day of treatment; and
    (c) administering intramuscularly in the deltoid or gluteal muscle of the patient in need of treatment a first maintenance dose of about 25 mg-eq. to about 150 mg-eq. of paliperidone as paliperidone palmitate in a sustained release formulation a month (±7 days) after the second loading dose.

5. The dosing regimen of claim 4 wherein the sustained release formulation is an aqueous nanoparticle suspension.

6. The dosing regimen of claim 4 wherein the psychiatric patient is in need of treatment for psychotic disorder wherein the psychotic disorder is schizophrenia.

7. The dosing regimen of claim 4 wherein the psychiatric patient is in need of treatment for a psychotic disorder wherein the psychotic disorder is schizoaffective disorder.

8. A dosing regimen for administering paliperidone palmitate to a renally impaired psychiatric patient in need of treatment for schizophrenia, schizoaffective disorder, or schizophreniform disorder comprising
  (a) administering intramuscularly in the deltoid of a renally impaired psychiatric patient in need of treatment a first loading dose of from about 75 mg-eq. of paliperidone as paliperidone palmitate formulated in a sustained release formulation on the first day of treatment;
  (b) administering intramuscularly in the deltoid muscle of the patient in need of treatment a second loading dose of from about 75 mg-eq. of paliperidone as paliperidone palmitate formulated in a sustained release formulation on the 6$^{th}$ to about 10th day of treatment; and
  (c) administering intramuscularly in the deltoid or gluteal muscle of the patient in need of treatment a first maintenance dose of about 25 mg-eq. to about 75 mg-eq. of paliperidone as paliperidone palmitate in a sustained release formulation a month (±7 days) after the second loading dose.

9. The dosing regimen of claim 8 wherein after the first maintenance dose, subsequent maintenance doses of from about 25 mg-eg. to 150 mg-eg. are administered in the deltoid or gluteal muscle of the psychiatric patient in need of treatment of monthly (±7) intervals.

10. The dosing regimen of claim 8 wherein the sustained release formulation is an aqueous nanoparticle suspension.

11. A dosing regimen for administering paliperidone palmitate to a renally impaired psychiatric patient in need of treatment for psychotic disorder comprising
  (a) administering intramuscularly in the deltoid of a renally impaired psychiatric patient in need of treatment a first loading dose of from about 75 mg-eq. of paliperidone as paliperidone palmitate formulated in a sustained release formulation on the first day of treatment;
  (b) administering intramuscularly in the deltoid muscle of the patient in need of treatment a second loading dose of from about 75 mg-eq. of paliperidone as paliperidone palmitate formulated in a sustained release formulation on the eighth day of treatment; and
  (c) administering intramuscularly in the deltoid or gluteal muscle of the patient in need of treatment a first maintenance dose of about 25 mg-eq. to about 50 mg-eq. of paliperidone as paliperidone palmitate in a sustained release formulation a month (±7 days) after the second loading dose.

12. The dosing regimen of claim 11 wherein the sustained release formulation is an aqueous nanoparticle suspension.

13. The dosing regimen of claim 11 wherein the psychiatric patient is in need of treatment for of a psychotic disorder wherein the psychotic disorder is schizophrenia.

14. The dosing regimen of claim 11 wherein the psychiatric patient is in need of treatment for a psychotic disorder wherein the psychotic disorder is schizoaffective disorder.

15. The dosing regimen of claim 4 wherein after administration of the first maintenance dose, subsequent maintenance doses of from about 25 mg-eq. to 150 mg-eq. are administered in the deltoid or gluteal muscle of the psychiatric patient in need of treatment at monthly (±7 days) intervals.

16. The dosing regimen of claim 11 wherein after administration of the first maintenance dose, subsequent maintenance doses of from about 25 mg-eq. to 150 mg-eq. are administered in the deltoid or gluteal muscle of the psychiatric patient in need of treatment at monthly (±7 days) intervals.

17. The dosing regimen of claim 1, 4, 8 or 11 wherein the formulation is an aqueous nanoparticle suspension comprises
  (a) from 3 to 20% (w/v) of the paliperidone palmitate having an average particle size (d50) of from about 1600 nm to about 900 nm;
  (b) from 0.5 to 3% (w/v) of a wetting agent wherein the wetting agent is polysorbate 20;
  (c) one or more buffering agents sufficient to render the composition neutral to very slightly basic (pH 8.5);
  (d) from 0.5 to 3% (w/v) of a suspending agent wherein the suspending agent is polyethylene glycol 4000; and
  (e) up to 2% (w/v) preservatives; and
  (f) water q.s. ad 100%.

18. The dosage regimen of claim 17 wherein the concentration of paliperidone palmitate is 156 mg/ml in the aqueous nanoparticle suspension.

19. The dosing regimen of claims 1, 4, 8 or 11 wherein the sustained release depot formulation is an aqueous nanoparticle suspension consists essentially of
  (a) 156 mg/ml of the paliperidone palmitate having an average particle size (d50) of from about 1600 nm to about 900 nm;
  (b) 12 mg/ml of polysorbate 20;
  (c) one or more buffering agents sufficient to render the composition neutral to very slightly basic (pH 8.5);
  (d) 30 mg/ml of a suspending agent wherein the suspending agent is polyethylene glycol 4000; and
  (f) water q.s. ad 100%.

20. The dosage regimen of claim 19 wherein in the buffering agents contained in the aqueous nanoparticle suspension are citric acid monohydrate, disodium hydrogen phosphate anhydrous, sodium dihydrogen phosphate monohydrate, sodium hydroxide.

21. The dosage regimen of claim 19 wherein in the pH of the aqueous nanoparticle suspension is in the range of pH 7 to 7.5.

* * * * *

UNITED STATES PATENT AND TRADEMARK OFFICE
CERTIFICATE OF CORRECTION

Page 1 of 1

PATENT NO. : 9,439,906 B2
APPLICATION NO. : 12/337144
DATED : September 13, 2016
INVENTOR(S) : An Vermeulen et al.

It is certified that error appears in the above-identified patent and that said Letters Patent is hereby corrected as shown below:

On the Title Page

Item (75) "Inventors" add:
"Srihari Gopal, Belle Mead, NJ (US)
Mahesh Samtani, Flemington, NJ (US)"

Signed and Sealed this
First Day of February, 2022

Drew Hirshfeld
*Performing the Functions and Duties of the*
*Under Secretary of Commerce for Intellectual Property and*
*Director of the United States Patent and Trademark Office*